US006406859B1

(12) United States Patent
Weinshank et al.

(10) Patent No.: US 6,406,859 B1
(45) Date of Patent: *Jun. 18, 2002

(54) DNA ENCODING A 5-HT 1F RECEPTOR AND USES THEREOF

(75) Inventors: Richard L. Weinshank; Theresa Branchek, both of Teaneck; Paul R. Hartig, Pennington, all of NJ (US)

(73) Assignee: Synaptic Pharmaceutical Corporation, Paramus, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/246,075

(22) Filed: Feb. 5, 1999

Related U.S. Application Data

(63) Continuation of application No. 08/483,222, filed on Jun. 7, 1995, now abandoned, which is a continuation of application No. 08/117,006, filed as application No. PCT/US93/00149 on Jan. 8, 1993, now Pat. No. 5,639,652, which is a continuation-in-part of application No. 07/817,920, filed on Jan. 8, 1992, now Pat. No. 5,360,735.

(51) Int. Cl.[7] .................. C12N 15/18; G01N 33/00; G01N 33/53

(52) U.S. Cl. .................. 435/7.1; 435/7.21; 435/7.2; 435/69.1; 435/320.1; 435/325

(58) Field of Search .................. 435/7.1, 7.2, 7.21, 435/69.1, 325, 320.1

(56) References Cited

U.S. PATENT DOCUMENTS

| | | |
|---|---|---|
| 5,155,218 A | 10/1992 | Weinshank et al. |
| 5,360,735 A | 11/1994 | Weinshank et al. |
| 5,472,866 A | 12/1995 | Gerald et al. |
| 5,476,782 A | 12/1995 | Weinshank et al. |
| 5,521,196 A | 5/1996 | Audia et al. |
| 5,559,143 A | 9/1996 | McDonald et al. |
| 5,652,113 A | * 7/1997 | Weinshank et al. |
| 5,661,024 A | 8/1997 | Kao et al. |
| 5,698,571 A | 12/1997 | Audia et al. |

FOREIGN PATENT DOCUMENTS

| | | |
|---|---|---|
| EP | 0351921 | 1/1990 |
| WO | 8908149 | 9/1989 |
| WO | 9117174 | 11/1991 |
| WO | 9311147 | 6/1993 |

OTHER PUBLICATIONS

Gerhardt, C. et al., *European Journal of Pharmacology*, 334(1):1–23, 1997.*

Adham, N., et al. Cloning of another human serotonin receptor (5–HT$_{1F}$): A fifth 5–HT$_1$ receptor subtype coupled to the inhibition of adenylate cyclase. Proc. Natl. Acad. Sci. U.S.A. 1993; 90:408–412.

Amlaiky, N., et al. Isolation of a mouse "5HT1E–like" serotonin receptor expressed predominantly in hippocampus. J. Biol. Chem. 1992; 267(28):19761–19764.

Leonhardt, S., et al. Detection of a Novel Serotonin Receptor Subtype (5–HT$_{1E}$) in Human Brain: Interaction with a GTP–Binding Protein. J. Neurochemistry 1989: 53(2):465–471.

Schwab, E. F., et al. Dominant spinal cord 5–HT receptor, 5–HT$_{1F}$: relation to pain. Soc. Neurosci. Abstr. 1989: 15(1):546.

Weisberg, E., et al. Novel High–Affinity $^3$H–Serotonin Binding Sites in Rat and Bovine Brain Tissue Drug Development Research 1992; 26:225–234.

Feniuk, W., et al. The Development of a Highly Selective 5–HT$_1$ Receptor Agonist, Sumatriptan, for the Treatment of Migraine. Drug Develpment Research 1992, 26:235–240.

Fargin, et al. Dual Coupling of the Cloned 5–HT$_{1A}$ Receptor to both Adenylyl Cyclase and Phospholipase C is Mediated Via The Same G$_1$ Protein. Cellular Signaling (1991) 3(6): 547–557 (Exhibit 7).

Foguet, et al. Structure of the mouse 5–HT$_{1C}$, 5–HT$_2$ and stomach fundus serotonin receptor genes. NeuroReport; Apr. 1992; 3(4): 345–348.

Hamblin, et al. Primary Structure and Function Characterization of a Human 5–HT1D–Type Serotonin Receptor. Mol. Pharmacol. (1991) 40: 143–148.

(List continued on next page.)

*Primary Examiner*—Marianne P. Allen
(74) *Attorney, Agent, or Firm*—John P. White; Cooper & Dunham LLP

(57) ABSTRACT

This invention provides an isolated nucleic acid molecule encoding a human 5-HT$_{1F}$ receptor, an isolated protein which is a human 5-HT$_{1F}$ receptor, vectors comprising an isolated nucleic acid molecule encoding a human 5-HT$_{1F}$ receptors, mammalian cells comprising such vectors, antibodies directed to the human 5-HT$_{1F}$ receptor, nucleic acid probes useful for detecting nucleic acid encoding human 5-HT$_{1F}$ receptors, antisense oligonucleotides complementary to any sequences of a nucleic acid molecule which encodes a human 5-HT$_{1F}$ receptor, pharmaceutical compounds related to human 5-HT$_{1F}$ receptors, and nonhuman transgenic animals which express DNA a normal or a mutant human 5-HT$_{1F}$ receptor. This invention further provides methods for determining ligand binding, detecting expression, drug screening, and treatment involving the human 5-HT$_{1F}$ receptor.

3 Claims, 14 Drawing Sheets

OTHER PUBLICATIONS

Levy, et al. Molecular cloning of a human gene (S31) encoding a novel serotonin receptor mediating inhibition of adenylyl cyclase. FEBS Letters; Jan. 1992; 296(2): 201–206.

McAllister, et al. Molecular cloning of a serotonin receptor from human brain (5HT1E): A fifth 5HT1–like subtype. Proceeding of the National Academy of Sciences; Jun. 1992; 89: 5517–5521.

Zgombick, et al. Human Gene S31 Encodes the Pharmacologically Defined Serotonin 5–Hydroxytryptamine$_{1E}$ Receptor. Mol. Pharmacol.; Aug. 1992; 42: 180–185.

* cited by examiner

TTGCATGCCTGCAGGTCGACTCTAGAGGATCCCCGGGTACCGAGCTCGAATTCCTTTGTT

-550        -530        -510

ATTTTGTCATGCTTCAAGCCTAGGAAAAGCCTAAGCAAACTCTTGGTGGGCTCTTTGTT

-490        -470        -450

ACATTCCAGCCCTTTGAATAAGGCCACTGGCTCTATCAGCTTTGAATATATAACTCAACTA

-430        -410        -390

GTCAGTCAGTAGTACTGAAACAGTTGTTACGGAGGCCTGCGTTATTGAGATCGGGCCTGC

-370        -350        -330

CACACTTTTAAACTTTTTCTGACATGGACAAGAGAAAAACCAATTCTATAATGGCAGAG

-310        -290        -270

ATTTCACTGAGTAACAAGCTAGAGTATCATTAAAAATTGTGTATTTAACCTATATTTTA

FIGURE 1B

```
-250                        -230                         -210
AGAAATGTTTGGAAGTACTGGCTTTTTTACTGTCTCATTAAATTTCTAAATAAAA

-190                        -170                         -150
AGGAAAACTAAAACCCTTCAATCTGAACCCTCATTTTTTAATCTATAGAATATTCTGGGTA

-130                        -110                         -90
AACATAACATACACTTTTTAAAATTATTCTGAAAGGAAGAGAAAAGTTCTGAAGCCCT

-70                         -50                          -30
CTCTGAACTGTTTTTCTCCTCCCTGTTACAGGTATCCATTTTTCAGCTATATTAATCT

-10                          10                          30
TTTAAAACAAAGAAAAATGGATTTCTTAAATTCATCTGATCAAAACTTGACCTCAGAGGAA
              M  D  F  L  N  S  S  D  Q  N  L  T  S  E  E
```

FIGURE 1C

```
           50                    70                    90
CTGTTAAACAGAATGCCATCCAAAATTCTGGTGTCCCTCACTCTGTCTGGGCTGGCACTG
 L  L  N  R  M  P  S  K  I  L  V  S  L  T  L  S  G  L  A  L 110                   130                   150
ATGACAACAACTATCAACTCCCTTGTGATCGCTGCAATTATTGTGACCCGGAAGCTGCAC
 M  T  T  T  I  N  S  L  V  I  A  A  I  I  V  T  R  K  L  H 170                   190                   210
CATCCAGCCAATTATTTAATTTGTTCCCTTGCAGTCACAGATTTTCTTGTGGCTGTCCTG
 H  P  A  N  Y  L  I  C  S  L  A  V  T  D  F  L  V  A  V  L 230                   250                   270
GTGATGCCCTTCAGCATTGTGTATATTGTGAGAGAGAGCTGGATTATGGGGCAAGTGGTC
 V  M  P  F  S  I  V  Y  I  V  R  E  S  W  I  M  G  Q  V  V 290                   310                   330
TGTGACATTTGGCTGAGTGTTGACATTACCTGCTGCACGTGCTCCATCTTGCATCTCTCA
 C  D  I  W  L  S  V  D  I  T  C  C  T  C  S  I  L  H  L  S
```

FIGURE 1D

```
                      350                    370                       390
GCTATAGCTTTGGATCGGTATCGAGCAATCACAGATGCTGTGTTGAGTATGCCAGGAAAAGG
 A  I  A  L  D  R  Y  R  A  I  T  D  A  V  E  Y  A  R  K  R 410                    430                       450
ACTCCAAAGCATGCTGGCATTATGATTACAATAGTTTGGATTATATCTGTTTTTATCTCT
 T  P  K  H  A  G  I  M  I  T  I  V  W  I  I  S  V  F  I  S 470                    490                       510
ATGCCTCCTCTATTCTGGAGGCACCAAGGAACTAGCAGAGATGATGAATGCATCATCAAG
 M  P  P  L  F  W  R  H  Q  G  T  S  R  D  D  E  C  I  I  K 530                    550                       570
CACGACCACATTGTTCCACCATTTACTCAACATTTGGAGCTTTCTACATCCCACTGGCA
 H  D  H  I  V  S  T  I  Y  S  T  F  G  A  F  Y  I  P  L  A
```

FIGURE 1E

```
                    610                         630
TTGATTTGATCCTTACTACAAATATAGAGCAGCAAAGACATTATACCACAAGAGA
 L  I  L  L  Y  Y  K  I  Y  R  A  A  K  T  L  Y  H  K  R
            650                         670                         690
CAAGCAAGTAGGATTGCAAAGGAGGAGGTGAATGGCCAAGTCCTTTGGAGAGTGGTGAG
 Q  A  S  R  I  A  K  E  E  V  N  G  Q  V  L  L  E  S  G  E
            710                         730                         750
AAAAGCACTAAATCAGTTCCACATCCTATGTACTAGAAAAGTCTTTATCTGACCCATCA
 K  S  T  K  S  V  S  T  S  Y  V  L  E  K  S  L  S  D  P  S
            770                         790                         810
ACAGACTTTGATAAAATTCATAGCACAGTGAGAAGTCTCAGGTCTGAATTCAAGCATGAG
 T  D  F  D  K  I  H  S  T  V  R  S  L  R  S  E  F  K  H  E
            830                         850                         870
AAATCTTGGAGAAGGCAAAAGATCTCAGGTACAAGAGAACGAAAGCAGCCACTACCCTG
 K  S  W  R  R  Q  K  I  S  G  T  R  E  R  K  A  A  T  T  L
```

FIGURE 1F

```
                               910                         930
GGATTAATCTCTGGGTGCATTTGTAATATGTTGGCTTCCTTTTTTGTAAAGAATTAGTT
 G  L  I  L  G  A  F  V  I  C  W  L  P  F  F  V  K  E  L  V
        950                        970                        990
GTTAATGTCTGTGACAAATGTAAATTTCTGAAGAATGTCCAATTTTTGGCATGGCTT
 V  N  V  C  D  K  C  K  I  S  E  E  M  S  N  F  L  A  W  L
                  1010                       1030                      1050
GGGTATCTCAATTCCCTTATAAATCCACTGATTACACAATCTTAATGAAGACTTCAAG
 G  Y  L  N  S  L  I  N  P  L  I  Y  T  I  F  N  E  D  F  K
        1070                       1090                     1110
AAGCATTCCAAAGCTTGTGCGATGTCGATGTTAGTTTTAAAATGTTT
 K  A  F  Q  K  L  V  R  C  R  C
```

FIGURE 2A

```
             1                                                          50
5HT1c        M.........  ..........  ...VNLGNAV  RSLLMHLIGL  LVWQFDISIS
5HT2         MDILCEENTS  LSSTTNSLMQ  LNDDTRLYSN  DFNSGEANTS  DAFNWTVDSE
5HT1Da       M.........  ..........  ..........  .....SPLN   QSAEGLPQEA
5HT1Dß       M.........  ..........  ..........  ..........  ..........
5HT1E        M.........  ..........  ..........  ..........  ..........
5HT1F        M.........  ..........  ..........  ..........  ..........
5HT1A        ..........  ..........  ..........  ..........  ..........
TM Region 51                                                         100
5HT1c        PVAAIVTDTF  NSSDGGRLFQ  FPDGVQNWPA  LSIVVIIMT   IGGNILVIMA
5HT2         NRTNLSCEGC  LSPSCLSLLH  LQE..KNWSA  LLTAVVILT   IAGNILVIMA
5HT1Da       ..SNRSLNA   TETSEAWDPR  TLQALKISLA  VVLSVITLAT  VLSNAFVLTT
5HT1Dß       NLSSAPSQNC  SAKDYIYQDS  ISLPWKVLLV  MLLALITLAT  TLSNAFVIAT
5HT1E        ....DFLNSS  DQNLTSEELL  NRMPSKILVS  LTLSGLALMT  TTINSLVIAA
5HT1F        NTTSPPAPFE  TGGNTTGISD  VTVSYQVITS  LLLGTLIFCA  VLGNACVVAA
5HT1A        ..........  ..........  ..........  ..*******   I..*******
TM Region 101                                                        150
5HT1c        VSMEKKLHNA  TNYFLMSLAI  ADMLVGLLVM  PLSLLAILYD  YVWPLPRYLC
5HT2         VSLEKKLQNA  TNYFLMSLAI  ADMLLGFLVM  PVSMLTILYG  YRWPLPSKLC
5HT1Da       ILLTRKLHTP  ANYLIGSLAT  TDLLVSILVM  PISMAYTITH  .TWNFGQILC
5HT1Dß       VYRTRKLHTP  ANYLIASLAV  TDLLVSILVM  PISTMYTVTG  .RWTLGQVVC
5HT1E        IIVTRKLHHP  ANYLICSLAV  TDFLVAVLVM  PFSIVYIVRE  .SWIMGQVVC
5HT1F        IALERSLQNV  ANYLIGSLAV  TDLMVSVLVL  PMAALYQVLN  .KWTLGQVTC
5HT1A        *.........  ..*******   ***..II..*  .*********  ..........
TM Region
```

FIGURE 2B

```
            151                                                         200
5HT_1c      PVWISLDVLF STASIMHLCA ISLDRYVAIR NPIEHSRFNS RTKAIMKIAI
5HT_2       AVWIYLDVLF STASIMHLCA ISLDRYVAIQ NPIHHSRFNS RTKAFLKIIA
5HT_1Da     DIWLSSDITC CTASILHLCV IALDRYWAIT DALEYSKRRT AGHAATMIAI
5HT_1Dβ     DFWLSSDITC CTASILHLCV IALDRYWAIT DAVEYSAKRT PKRAAVMIAL
5HT_1F      DIWLSVDITC CTCSILHLSA IALDRYRAIT DAVEYARKRT PKHAGIMITI
5HT_1A      DLFIALDVLC CTSSILHLCA IALDRYWAIT DPIDYVNKRT PRRAAALISL
TM Region   .********. .***          .III..****   ......     ******

201                                                         250
5HT_1c      VWAISIGVSV PIPVIGLRDE SKVFVNNTTC VLNDP.NFVL IGSFVAFFIP
5HT_2       VWTISVGISM PIPVFGLQDD SKVF.KEGSC LLADD.NFVL IGSFVSFFIP
5HT_1Da     VWAISICISI P.PLF.WRQA KAQEEMSDCL VNTSQISYTI YSTCGAFYIP
5HT_1Dβ     VWVFSISISL P.PFF.WRQA KAEEEVSECV VNTDHILYTV YSTVGAFYFP
5HT_1F      VWIISVFISM P.PLF.WRHQ GTSRD.DECI IKHDHIVSTI YSTFGAFYIP
5HT_1A      TWLIGFLISI P.PMLGWRTP EDRSDPDACT ISKDH.GYTI YSTFGAFYIP
TM Region   ***..IV..*  ********          ...                   ***   ......V.

```
                                                                                          350
5HT1C        LTIMVITYFL TI.....YVL RRQTLMLLRG .HTEEELANM SLNFLNCCCK
5HT2         LTIMVITYFL TI.....KSL QKEATLCVSD LGTRAKLA.. SFSFLPQSSL
5HT1Dα       SVLLILYGR  IYRAARNRIL .NPPSLYGKR FTTAHLITGS .G..SSLCSL
5HT1Dβ       TLLLIALYGR IYVEARSRIL KQTPNRTGKR LTRAQLITDS PGSTSSVTSI
5HT1F        LALILILYYK IYRAAKTLYH KRQASRIAKE EVNGQVLLES GE..KSTKSV
5HT1A        LLLMLVLYGR IFRAARFRIR KTVKKVEKTG ADTRHGASPA PQPKKSVNGE
TM Region    .******... ..........

301
5HT1C        KNGGEEENAP NPNPDQ..KP RRKKKEKRPR GTMQ......
5HT2         SSEKLFQRSI HREPGS..YT GRR....... .TMQ......
5HT1Dα       NSS..LHEGH SHSAGSPLFF N.HVKIKLAD SALE......
5HT1Dβ       NSR..VPDVP SES.GSPVYV N.QVKVRVSD ALLE......
5HT1F        STS..YVLEK SLSDPSTDFD KIHSTVRSLR SEFKHEKSWR
5HT1A        SGSRNWRLGV ESKAGGALCA NGAVRQGDDG AALEVIEVHR VGNSKEHLPL
TM Region 400
             351
5HT1C        .......... .......... .......AI NNEKKASKVL GIVFFVFLIM
5HT2         .......... .......... ........SI SNEQKACKVL GIVFFLFVVM
5HT1Dα       .......... .......... ....RKRISA ARERKATKIL GIILGAFIIC
5HT1Dβ       .......... .......... ....KKKLMA ARERKATKTL GIILGAFIVC
5HT1F        .......... .......... ....RQKISG TRERKAATTL GLILGAFVIC
5HT1A        PSEAGPTPCA PASFERKNER NAEAKRKMAL ARERKTVKTL GIIMGTFILC
TM Region    .......... .......... .........* .......... ********..
```

FIGURE 2D

```
              401                                                                      450
5HT1C         WCPFFITNIL  SVLCGGKACNQ  KLMEKLLNVF  VWIGYVCSGI  NPLVYTLFNK
5HT2          WCPFFITNIM  AVICKESCNE   DVIGALLNVF  VWIGYLSSAV  NPLVYTLFNK
5HT1Dα        WLPFFVVSLV  LPICRDSCW.   .IHPGLFDFF  TWLGYLNSLI  NPIIYTVFNE
5HT1Dβ        WLPFFIISLV  MPICKDACW.   .FHLAIFDFF  TWLGYLNSLI  NPIIYTMSNE
5HT1F         WLPFFVKELV  VNVC.DKCK.   .ISEEMSNFL  AWLGYLNSLI  NPLIYTIFNE
5HT1A         WLPFFIVALV  LPFCESSCH.   .MPTLLGAII  NWLGYSNSLL  NPVIYAYFNK
TM Region     VI..******  **......     ...******  ***..VII..  ........

451                                                                      500
5HT1C         IYRRAFSKYL  RCDYKPDKKP   .PVRQIPRVA  ATALSGRELN  VNIYRHTNER
5HT2          TYRSAFSRYI  QCQYKENKKP   LQLILVNTIP  ALAYKSSQLQ  MGQKKNSKQD
5HT1Dα        EFRQAFQKIV  PFRKAS....   ..........  ..........  ..........
5HT1Dβ        DFKQAFHKLI  RFICCTS...   ..........  ..........  ..........
5HT1F         DFKKAFQKLV  RCRC......   ..........  ..........  ..........
5HT1A         DFQNAFKKII  KCLFCRQ...   ..........  ..........  ..........
TM Region     .........   ..........   ..........  ..........  ..........

501                                537
5HT1C         VARKANDPEP  GIEMQVENLE   LPVNPSNVVS  ERISSV.
5HT2          AKTTDNDCSM  VALGKQHSEE   ASKDNSDGVN  EKVSCV.
5HT1Dα        ..........  ..........   ..........  .......
5HT1Dβ        ..........  ..........   ..........  .......
5HT1F         ..........  ..........   ..........  .......
5HT1A         ..........  ..........   ..........  .......
TM Region     ..........  ..........   ..........  .......
```

Brain

Testes
Endometrium
Mesentery
Myometrium
Pancreas
Kidney
Liver
Spleen
Heart
H₂O

Control

DNA ENCODING A 5-HT 1F RECEPTOR AND USES THEREOF

This application is a continuation of U.S. Ser. No. 08/483,222, filed Jun. 7, 1995, now abandoned which is a continuation of U.S. Ser. No. 08/117,006, filed Aug. 22, 1994, now U.S. Pat. No. 5,639,652, which is the 371 national stage filing of PCT International Application No. PCT/US93/00149, filed Jan. 8, 1993, which is a continuation-in-part of U.S. Ser. No. 07/817,920, filed Jan. 8, 1992, now U.S. Pat. No. 5,360,735.

BACKGROUND OF THE INVENTION

Throughout this application various publications are referenced by partial citations within parentheses. The disclosures of these publications in their entireties are hereby incorporated by reference in this application in order to more fully describe the state of the art to which this invention pertains.

Since the purification of a pressor substance in blood serum termed serotonin (Rapport et al., 1947) and later identified as 5-hydroxytryptamine (5-HT) (Rapport, 1949), there has been a plethora of reports demonstrating that this indoleamine not only plays a role in the functioning of peripheral tissues but, indeed, performs a key role in the brain as a neurotransmitter. Certainly, the anatomical localization of serotonin and serotonergic neurons in both the peripheral and central nervous systems supports its role in such diverse physiologic and behavioral functions as pain perception, sleep, aggression, sexual activity, hormone secretion, thermoregulation, motor activity, cardiovascular function, food intake and renal regulation (For review see Green, 1985; Osborne and Hamon, 1988; Sanders-Bush, 1988; Peroutka, 1991). Taken together, it appears that serotonin plays an important role in homeostasis and in modulating responsiveness to environmental stimuli. Accordingly, studies demonstrating that abnormalities in the serotonergic system may be associated with disease states has created a drug development effort towards agents which may selectively modulate the function of serotonin (Glennon, 1990).

In relation to the characterization of physiologic or biochemical responses resulting from the release of serotonin are simultaneous investigation examining the receptor sites responsible for the actions elicited by the indoleamine transmitter. Following early in vitro pharmacological assays describing the existence of two different serotonin receptors, designated as D and M, in the guinea pig ileum (Gaddum and Picarelli, 1957), the advent of receptor binding technique in the 1970's has brought to light during the last decade the diversity of 5-HT receptors existing in both the brain and peripheral tissues. Thus, although the concept of D and M receptors has not been invalidated, serotonin receptors not fitting either category have been identified using radioligand methods. To date using this technique, there appears to be four classes of serotonin receptors found in the brain: 5-HT$_1$, 5-HT$_2$, 5-HT$_3$ and, putatively, 5-HT$_4$ (Peroutka, 1991). Furthermore, 5-HT$_1$ sites have been subclassified as: 5-HT$_{1A}$, 5-HT$_{1B}$, 5-HT$_{1C}$, 5-HT$_{1D}$ (Hamon et al., 1990) and 5-HT$_{1E}$ (Leonhardt et al., 1989). Although a detailed characterization of the 5-HT$_{1F}$ binding site is lacking, extensive pharmacologic, biochemical and functional properties have clearly shown that the other four subtypes of 5-HT$_1$ sites are receptors according to classical criteria.

During the last few years, the field of molecular biology has provided an important facet to receptor research by cloning these proteins and allowing more precise characterizations in isolated systems (Hartig et al,1990). This has been accomplished for the 5-HT$_{1A}$ (Fargin et al., 1988), 5-HT$_{1C}$ (Julius et al., 1988), 5-HT$_{1D}$ (Branchek et al., 1990) and 5-HT$_2$ receptors (Pritchett et al., 1988). Thus, there is no doubt that these binding sites represent "true" functional receptors. Indeed, the pharmacological characterization of serotonin receptors involved in various physiological or biochemical functions is a key component of drug development for the serotonergic system. As one can deduce from the diversity of serotonin binding sites, many targets are available for advancement in selective drug design. The coupling of molecular biological methods to pharmacological characterization particularly for cloned human receptors will open new avenues for pharmaceutical development which has not been previously explored.

This study is a pharmacological characterization of a serotonergic receptor clone with a binding profile different from that of any serotonergic receptor to date. In keeping with the nomenclature presently accepted for serotonin receptors, this novel site will be termed a 5-HT$_{1F}$ receptor based upon the fact that it possesses high affinity for the endogenous neurotransmitter, 5-HT.

SUMMARY OF THE INVENTION

This invention provides an isolated nucleic acid molecule encoding a human 5-HT$_{1F}$ receptor (Seq. I.D. No. 1).

This invention also provides an isolated protein which is a human 5-HT$_{1F}$ receptor (Seq. I.D. Nos. 2, 7).

This invention provides a vector comprising an isolated nucleic acid molecule encoding a human 5-HT$_{1F}$ receptor.

This invention also provides vectors such as plasmids comprising a DNA molecule encoding a human 5-HT$_{1F}$ receptor, adapted for expression in a bacterial cell, a yeast cell, or a mammalian cell which additionally comprise the regulatory elements necessary for expression of the DNA in the bacterial, yeast, or mammalian cells so located relative to the DNA encoding the 5-HT$_{1F}$ receptor as to permit expression thereof.

This invention provides a mammalian cell comprising a DNA molecule encoding a human 5-HT$_{1F}$ receptor.

This invention provides a method for determining whether a ligand not known to be capable of binding to a human 5-HT$_{1F}$ receptor can bind to a human 5-HT$_{1F}$ receptor which comprises contacting a mammalian cell comprising an isolated DNA molecule encoding a human 5-HT$_{1F}$ receptor with the ligand under conditions permitting binding of ligands known to bind to a 5-HT$_{1F}$ receptor, detecting the presence of any of the ligand bound to a human 5-HT$_{1F}$ receptor, and thereby determining whether the ligand binds to a human 5-HT$_{1F}$ receptor.

This invention also provides a method for determining whether a ligand not known to be capable of binding to the human 5-HT$_{1F}$ receptor can functionally activate its activity or prevent the action of a ligand which does so. This comprises contacting a mammalian cell comprising an isolated DNA molecule which encodes a human 5-HT$_{1F}$ receptor with the ligand under conditions permitting the activation of blockade of a functional response, detected by means of bioassay from the mammalian cell such as a second messenger response, and thereby determining whether the ligand activates or prevents the activation of the human 5-HT$_{1F}$ receptor functional output.

This invention further provides a method of screening drugs to identify drugs which specifically interact with, and bind to, the human 5-HT$_{1F}$ receptor on the surface of a cell which comprises contacting a mammalian cell comprising an isolated DNA molecule encoding a human 5-HT$_{1F}$ receptor with a plurality of drugs, determining those drugs which bind to the mammalian cell, and thereby identifying drugs which specifically interact with, and bind to, a human 5-HT$_{1F}$ receptor.

This invention also provides a method of screening drugs to identify drugs which interact with, and activate or block the activation of, the human 5-HT$_{1F}$ receptor on the surface of a cell which comprises contacting the mammalian cell comprising an isolated DNA molecule encoding and expressing a human 5-HT$_{1F}$ receptor with a plurality of drugs, determining those drugs which activate or block the activation of the receptor in the mammalian cell using a bioassay such as a second messenger assays, and thereby identifying drugs which specifically interact with, and activate or block the activation of, a human 5-HT$_{1F}$ receptor.

This invention provides a nucleic acid probe comprising a nucleic acid molecule of at least 15 nucleotides capable of specifically hybridizing with a sequence included within the sequence of a nucleic acid molecule encoding a human 5-HT$_{1F}$ receptor.

This invention also provides a method of detecting expression of the 5-HT$_{1F}$ receptor on the surface of a cell by detecting the presence of mRNA coding for a 5-HT$_{1F}$ receptor which comprises obtaining total mRNA from the cell and contacting the mRNA so obtained with a nucleic acid probe comprising a nucleic acid molecule of at least 15 nucleotides capable of specifically hybridizing with a sequence included within the sequence of a nucleic acid molecule encoding a human 5-HT$_{1F}$ receptor under hybridizing conditions, detecting the presence of mRNA hybridized to the probe, and thereby detecting the expression of the 5-HT$_{1F}$ receptor by the cell.

This invention provides an antisense oligonucleotide having a sequence capable of binding specifically with any sequences of an mRNA molecule which encodes a human 5-HT$_{1F}$ receptor so as to prevent translation of the mRNA molecule.

This invention provides an antibody directed to a human 5-HT$_{1F}$ receptor.

This invention provides a transgenic nonhuman mammal expressing DNA encoding a human 5-HT$_{1F}$ receptor. This invention also provides a transgenic nonhuman mammal expressing DNA encoding a human 5-HT$_{1F}$ receptor so mutated as to be incapable of normal receptor activity, and not expressing native 5-HT$_{1F}$ receptor. This invention further provides a transgenic nonhuman mammal whose genome comprises antisense DNA complementary to DNA encoding a human 5-HT$_{1F}$ receptor so placed as to be transcribed into antisense mRNA which is complementary to mRNA encoding a 5-HT$_{1F}$ receptor and which hybridizes to mRNA encoding a 5-HT$_{1F}$ receptor thereby reducing its translation.

This invention provides a method of determining the physiological effects of expressing varying levels of human 5-HT$_{1F}$ receptors which comprises producing a transgenic nonhuman animal whose levels of human 5-HT$_{1F}$ receptor expression are varied by use of an inducible promoter which regulates human 5-HT$_{1F}$ receptor expression.

This invention also provides a method of determining the physiological effects of expressing varying levels of human 5-HT$_{1F}$ receptors which comprises producing a panel of transgenic nonhuman animals each expressing a different amount of human 5-HT$_{1F}$ receptor.

This invention provides a method for diagnosing a predisposition to a disorder associated with the expression of a specific human 5-HT$_{1F}$ receptor allele which comprises: a. obtaining DNA of subjects suffering from the disorder; b. performing a restriction digest of the DNA with a panel of restriction enzymes; c. electrophoretically separating the resulting DNA fragments on a sizing gel; d. contacting the resulting gel with a nucleic acid probe capable of specifically hybridizing to DNA encoding a human 5-HT$_{1F}$ receptor and labelled with a detectable marker; e. detecting labelled bands which have hybridized to the DNA encoding a human 5-HT$_{1F}$ receptor labelled with a detectable marker to create a unique band pattern specific to the DNA of subjects suffering from the disorder; f. preparing DNA obtained for diagnosis by steps a–e; and g. comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method of preparing the isolated 5-HT$_{1F}$ receptor which comprises inducing cells to express 5-HT$_{1F}$ receptor, recovering the receptor from the resulting cells and purifying the receptor so recovered.

This invention also provides a method of preparing the isolated 5-HT$_{1F}$ receptor which comprises inserting nucleic acid encoding 5-HT$_{1F}$ receptor in a suitable vector, inserting the resulting vector in a suitable host cell, recovering the receptor produced by the resulting cell, and purifying the receptor so recovered.

This invention provides an antisense oligonucleotide having a sequence capable of binding specifically with any sequences of an mRNA molecule which encodes a receptor so as to prevent translation of the mRNA molecule.

This invention also provides a transgenic nonhuman mammal expressing DNA encoding a receptor.

This invention further provides a transgenic nonhuman mammal expressing DNA encoding a receptor so mutated as to be incapable of normal receptor activity, and not expressing native receptor.

This invention also provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides a transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

BRIEF DESCRIPTION OF THE FIGURES

FIG. 1. (FIGS. 1A–1F) Nucleotide and deduced amino acid sequence of gene 5-HT$_{1F}$ (Seq. I.D. Nos. 1, 2, and 7).

Numbers above the nucleotide sequence indicate nucleotide position. DNA sequences was determined by the chain termination method of Sanger, et al., on denatured double-stranded plasmid templates using the enzyme Sequenase. Deduced amino acid sequence (single letter code) of a long open reading frame is shown.

FIG. 2. (FIGS. 2A–2D) Comparison of the human 5-HT$_{1F}$ receptor primary structures with other serotonin receptors (Seq. I.D. Nos.: 5-HT$_{1A}$- 3; 5-HT$_{1C}$- 4; 5-HT$_{1D\alpha}$- 5; 5-HT$_{1D\beta}$- 6; 5-HT$_{1F}$- 7; 5-HT$_2$- 8).

Amino acid sequences (single letter code) are aligned to optimize homology. The putative transmembrane spanning domains are indicated by stars and identified by Roman numerals (TM I–VIII).

Figure 3:
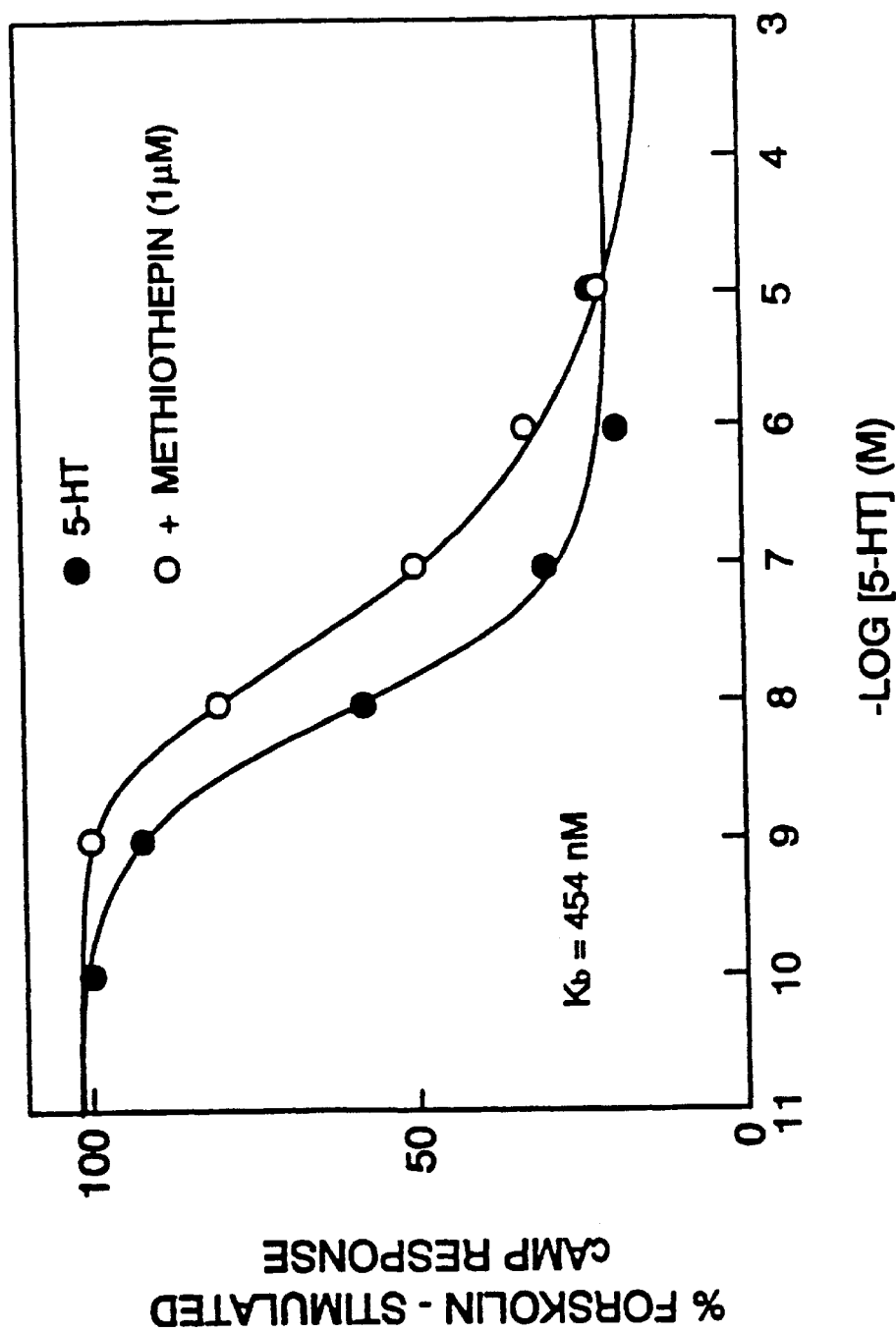

FIG. 3. 5-HT concentration-effect curves are represented in the absence (.) and in the presence (o) of methiothepin (1.0 $\mu$M). Data were normalized to 100% relative to forskolin-stimulated values in the absence of agonist to derive values of $E_{max}$ and $E_{50}$. The antagonist $K_b$ was estimated by method of Furchgott (32): $K_b$=(Dose of antagonist)/(($E_{50}$ in the presence of antagonist/control $E_{50}$) −1).

Figure 4:

FIG. 4. Human tissue distribution of RNA coding for 5-HT$_{1F}$ receptor gene. Total RNA was converted to single-stranded cDNA by random-priming with reverse transcriptase. cDNAs were amplified by PCR using 5-HT$_{1F}$ specific PCR primers. PCR products were run on a 1.5% agarose gel, blotted onto nylon membranes and hybridized to internal gene-specific oligonucleotides and washed under high stringency. Positive represent gene-specific recombinant plasmids; dH$_2$O served as a negative control. PCR amplification and Southern blotting of RNA samples not treated with reverse transcriptase were negative.

FIG. 5: 5-HT$_{1F}$ receptor mRNA in the guinea pig brain coronal sections. A. An antisense oligonucleotide probe (4,5 loop) was used. An identical pattern was observed with the 5' untranslated probe (not illustrated). Hybridization densities are high in layer V of cerebral cortex (V), and in CA1–CA3 of the hippocampus (HC). B. Control contralateral hemisphere of an adjacent section to that in A. No hybridization was seen using a sense probe of identical specific activity. C. Section hybridized with the antisense probe. The dorsal raphe (DR) is densely labeled. D. At high magnification, hybridization (antisense probe) is detected in layer V of sensorimotor cortex. Arrowheads indicate heavily labeled pyramidal cells. E. As in D, through the dorsal raphe. Arrowheads indicate large, heavily labeled neurons. Magnification in panels D and E=X270.

DETAILED DESCRIPTION OF THE INVENTION

As used herein, the 5-HT receptor family is defined as the group of mammalian proteins that function as receptors for serotonin. A 5-HT receptor subfamily is defined as a subset of proteins belonging to the 5-HT receptor family which are encoded by genes which exhibit homology of greater than 72% or higher with each other in their deduced amino acid sequences within presumed transmembrane regions (linearly contiguous stretches of hydrophobic amino acids, bordered by charged or polar amino acids, that are long enough to form secondary protein structures that span a lipid bilayer). Four human 5-HT receptor subfamilies can be distinguished based on the information presently available: 5-HT$_1$, 5-HT$_2$, 5-HT$_3$, and 5-HT$_4$ (Peroutka, 1991). The 5-HT$_2$ receptor subfamily contains the human 5-HT$_2$ receptor. Although no other human members of this family have been described, the rat 5-HT$_2$ receptor (Pritchett, et al. 1988; Julius, et al. Proc. Natl. Acad. Sci. USA 87:928–932, 1990) and the rat 5-HT$_{1C}$ receptor (Julius, et al. 1988) constitute a rat 5-HT receptor subfamily. The 5-HT$_1$ subfamily has been subdivided further as: 5-HT$_{1A}$, 5-HT$_{1B}$, 5-HT$_{1C}$, 5-HT$_{1D}$ (Hamon et al., 1990) and 5-HT$_{1E}$ (Leonhardt et al., 1989). The 5-HT$_{1A}$ subfamily contains the human 5-HT$_{1A}$ receptor, also known as G-21 (Fargin, et al. 1988) The 5-HT$_{1D}$ receptor subfamily contains two members, the 5-HT$_{1D-1}$ receptor (also termed 5-HT$_{1D\alpha}$) and the 5-HT$_{1D-2}$ receptor (also termed 5-HT$_{1D\beta}$). The 5-HT$_{1F}$ subfamily contains the human 5-HT$_{1F}$ receptor (also termed clone hl16a). Although this definition differs from the pharmacological definition used earlier, there is significant overlap between the present definition and the pharmacological definition. Members of the 5-HT$_{1F}$ receptor subfamily so described include the 5-HT$_{1F}$ receptor and any other receptors which have a greater than 72% homology to the DNA and amino acid sequence shown in FIG. 1 (Seq. I.D. Nos. 1, 2, and 7) according to the definition of "subfamily". This invention relates to the discovery of the first member of the human 5-HT$_{1F}$ receptor subfamily.

This invention provides an isolated nucleic acid molecule encoding a human 5-HT$_{1F}$ receptor (Seq. I.D. No. 1). As used herein, the term "isolated nucleic acid molecule" means a nucleic acid molecule that is, a molecule in a form which does not occur in nature. Such a receptor is by definition a member of the 5-HT$_{1F}$ receptor subfamily. Therefore, any receptor which meets the defining criteria given above is a human 5-HT$_{1F}$ receptor. One means of isolating a human 5-HT$_{1F}$ receptor is to probe a human genomic library with a natural or artificially designed DNA probe, using methods well known in the art. DNA probes derived from the human receptor gene 5-HT$_{1F}$ are particularly useful probes for this purpose. DNA and cDNA molecules which encode human 5-HT$_{1F}$ receptors may be used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clones, and other stability, processing, transcription, translation, and tissue specificity-determining regions from the 3' and 5' untranslated regions of the isolated genes are thereby obtained. Examples of a nucleic acid molecule are an RNA, cDNA, or isolated genomic DNA molecule according a human 5-HT$_{1F}$ receptor. Such molecules may have coding sequences substantially the same as the coding sequence shown in FIG. 1. The DNA molecule of FIG. 1 encodes the sequence of the human 5-HT$_{1F}$ receptor gene (Seq. I.D. No. 1).

This invention further provides a cDNA molecule of encoding a human 5-HT$_{1F}$ receptor having a coding sequence substantially the same as the coding sequence shown in FIG. 1 (Seq. I.D. No. 1). This molecule is obtained by the means described above.

This invention also provides an isolated protein which is a human 5-HT$_{1F}$ receptor. As used herein, the term "isolated protein means a protein molecule free of other cellular components. An example of such protein is an isolated protein having substantially the same amino acid sequence as the amino acid sequence shown in FIG. 1 (Seq. I.D. Nos. 2, 7) which is a human 5-HT$_{1F}$ receptor. One means for obtaining isolated 5-HT$_{1F}$ receptor is to express DNA encoding the receptor in a suitable host, such as a bacterial, yeast, or mammalian cell, using methods well known in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising an isolated nucleic acid molecule such as DNA, RNA, or cDNA encoding a human 5-HT$_{1F}$ receptor. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available. A specific example of such plasmids is a plasmid comprising cDNA having a coding sequence substantially the same as the coding sequence shown in FIG. 1 and designated clone hl16a.

This invention also provides vectors comprising a DNA molecule encoding a human 5-HT$_{1F}$ receptor, adapted for expression in a bacterial cell, a yeast cell, or a mammalian cell which additionally comprise the regulatory elements necessary for expression of the DNA in the bacterial, yeast, or mammalian cells so located relative to the DNA encoding a human 5-HT$_{1F}$ receptor as to permit expression thereof. DNA having coding sequences substantially the same as the coding sequence shown in FIG. 1 may usefully be inserted into the vectors to express human 5-HT$_{1F}$ receptors. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the receptor. Certain uses for such cells are described in more detail below.

This invention further provides a plasmid adapted for expression in a bacterial, yeast, or, in particular, a mammalian cell which comprises a DNA molecule encoding a human 5-HT$_{1F}$ receptor and the regulatory elements necessary for expression of the DNA in the bacterial, yeast, or mammalian cell so located relative to the DNA encoding a human 5-HT$_{1F}$ receptor as to permit expression thereof. Some plasmids adapted for expression in a mammalian cell are pSVL (available from Pharmacia, Piscataway, N.J.), pcEXV-3 (Miller J. and Germain R. N., J. Exp. Med. 164:1478 (1986)) and pMO5 (Branchek, T. et al, Mol. Pharm. 38:604–609 (1990)). A specific example of such plasmid is a plasmid adapted for expression in a mammalian cell comprising cDNA having coding sequences substantially the same as the coding sequence shown in FIG. 1 and the regulatory elements necessary for expression of the DNA in the mammalian cell which is designated pMO5-hl16a and deposited under ATCC Accession No. 75175. Those skilled in the art will readily appreciate that numerous plasmids adapted for expression in a mammalian cell which comprise DNA of encoding human 5-HT$_{1F}$ receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposit discussed supra, and the other deposits discussed herein, were made pursuant to, and in satisfaction of, the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a human 5-HT$_{1F}$ receptor, such as a mammalian cell comprising a plasmid adapted for expression in a mammalian cell, which comprises a DNA molecule encoding a human 5-HT$_{1F}$ receptor, the protein encoded thereby is expressed on the cell surface, and the regulatory elements necessary for expression of the DNA in the mammalian cell so located relative to the DNA encoding a human 5-HT$_{1F}$ receptor as to permit expression thereof. Numerous mammalian cells may be used as hosts, including, for example, the mouse fibroblast cell NIH3T3, CHO cells, HeLa cells, Ltk$^-$ cells, Y1 cells, etc. A particular example of an Ltk$^-$ cell is a cell designated L-5-HT$_{1F}$ and deposited under ATCC Accession No. CRL 10957 and comprises the plasmid designated pMO5-hl16a. Another example is the murine fibroblast cell line designated N-5-HT$_{1F}$ and deposited under ATCC Accession No. CRL 10956. Expression plasmids such as that described supra may be used to transfect mammalian cells by methods well known in the art such as calcium phosphate precipitation, or DNA encoding these 5-HT$_{1F}$ receptors may be otherwise introduced into mammalian cells, e.g., by microinjection, to obtain mammalian cells which comprise DNA, e.g., cDNA or a plasmid, encoding either human 5-HT$_{1F}$ receptor.

This invention provides a method for determining whether a ligand not known to be capable of binding to a human 5-HT$_{1F}$ receptor can bind to a human 5-HT$_{1F}$ receptor which comprises contacting a mammalian cell comprising a DNA molecule encoding a human 5-HT$_{1F}$ receptor, the protein encoded thereby is expressed on the cell surface, with the ligand under conditions permitting binding of ligands known to bind to the 5-HT$_{1F}$ receptor, detecting the presence of any of the ligand bound to the 5-HT$_{1F}$ receptor, and thereby determining whether the ligand binds to the 5-HT$_{1F}$ receptor. This invention also provides a method for determining whether a ligand not known to be capable of binding to the human 5-HT$_{1F}$ receptor can functionally activate its activity or prevent the action of a ligand which does so. This comprises contacting a mammalian cell comprising an isolated DNA molecule which encodes a human 5-HT$_{1F}$ receptor with the ligand under conditions permitting the activation or blockade of a functional response, detected by means of a bioassay from the mammalian cell such as a second messenger response, and thereby determining whether the ligand activates or prevents the activation of the human 5-HT$_{1F}$ receptor functional output. The DNA in the cell may have a coding sequence substantially the same as the coding sequence shown in FIG. 1 preferably, the mammalian cell is nonneuronal in origin. An example of a nonneuronal mammalian cell is an Ltk⁻ cell, in particular the Ltk⁻ cell designated L-5-HT$_{1F}$. Another example of a nonneuronal mammalian cell to be used for functional assays is a murine fibroblast cell line, specifically the NIH3T3 cell designated N-5-HT$_{1F}$. The preferred method for determining whether a ligand is capable of binding to the human 5-HT$_{1F}$ receptor comprises contacting a transfected nonneuronal mammalian cell (i.e. a cell that does not naturally express any type of 5-HT or G-protein coupled receptor, thus will only express such a receptor if it is transfected into the cell) expressing a 5-HT$_{1F}$ receptor on its surface, or contacting a membrane preparation derived from such a transfected cell, with the liquid under conditions which are known to prevail, and thus to be associated with, in vivo binding of the ligands to a 5-HT$_{1F}$ receptor, detecting the presence of any of the ligand being tested bound to the 5-HT$_{1F}$ receptor on the surface of the cell, and thereby determining whether the ligand binds to, activates or prevents the activation on the 5-HT$_{1F}$ receptor. This response system is obtained by transfection of isolated DNA into a suitable host cell containing the desired second messenger system such as phospholnositide hydrolysis, adenylate cyclase, guanylate cyclase or ion channels. Such a host system is isolated from pre-existing cell lines, or can be generated by inserting appropriate components of second messenger systems into existing cell lines. Such a transfection system provides a complete response system for investigation or assay of the activity of human 5-HT$_{1F}$ receptors with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the human 5-HT$_{1F}$ receptor. The transfection system is also useful for determining the affinity and efficacy of known drugs at the human 5-HT$_{1F}$ receptor sites.

This invention also provides a method of screening drugs to identify drugs which specifically interact with, and bind to, the human 5-HT$_{1F}$ receptor on the surface of a cell which comprises contacting a mammalian cell comprising a DNA molecule encoding a human 5-HT$_{1F}$ receptor on the surface of a cell with a plurality of drugs, determining those drugs which bind to the mammalian cell, and thereby identifying drugs which specifically interact with, and bind to, the human 5-HT$_{1F}$ receptor. This invention also provides a method of screening drugs to identify drugs which interact with, and activate or block the activation of, the human 5-HT$_{1F}$ receptor on the surface of a cell which comprises contacting the mammalian cell comprising an isolated DNA molecule encoding and expressing a human 5-HT$_{1F}$ receptor with a plurality of drugs, determining those drugs which activate or block the activation of the receptor in the mammalian cell using a bioassay such as a second messenger assays, and thereby identifying drugs which specifically interact with, and activate or block the activation of, a human 5-HT$_{1F}$ receptor. The DNA in the cell may have a coding sequence substantially the same as the coding sequence shown in FIG. 1 (Seq. I.D. No. 1). Preferably, the mammalian cell is nonneuronal in origin. An example of a nonneuronal mammalian cell is an Ltk⁻ cell, in particular the Ltk⁻ cell designated L-5-HT$_{1F}$. Another example of a nonneuronal mammalian cell to be used for functional assays is a murine fibroblast cell line, specifically the NIH3T3 cell designated N-5-HT$_{1F}$. Drug candidates are identified by choosing chemical compounds which bind with high affinity to the expressed 5-HT$_{1F}$ receptor protein in transfected cells, using radioligand binding methods well known in the art, examples of which are shown in the binding assays described herein. Drug candidates are also screened for selectivity by identifying compounds which bind with high affinity to one particular 5-HT$_{1F}$ receptor subtype but do not bind with high affinity to any other serotonin receptor subtype or to any other known receptor site. Because selective, high affinity compounds interact primarily with the target 5-HT$_{1F}$ receptor site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

This invention provides a nucleic acid probe comprising a nucleic acid molecule of at least 15 nucleotides capable of specifically hybridizing with a sequence included within the sequence of a nucleic acid molecule encoding a human 5-HT$_{1F}$ receptor, for example with a coding sequence included within the sequence shown in FIG. 1. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding human 5-HT$_{1F}$ receptors is useful as a diagnostic test for any disease process in which levels of expression of the corresponding 5-HT$_{1F}$ receptor is altered. DNA probe molecules are produced by insertion of a DNA molecule which encodes human 5-HT$_{1F}$ receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. An example of such DNA molecule is shown in FIG. 1. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes human 5-$HT_{1F}$ receptor of are useful as probes for these genes, for their associated mRNA, or for the isolation of related genes by homology screening of genomic or cDNA libraries, or by the use of amplification techniques such as the Polymerase Chain Reaction. Synthesized oligonucleotides as described may also be used to determine the cellular localization of the mRNA produced by the 5-$HT_{1F}$ gene by in situ hybridization. An example of such an oligonucleotide is: 5'-TCTCACCACTCTCCAAAAGGA-CTTGGCCATTCACCTCCTCCTTTG-3' (Seq. I.D. No. 9).

This invention also provides a method of detecting expression of a 5-$HT_{1F}$ receptor on the surface of a cell by detecting the presence of mRNA coding for a 5-$HT_{1F}$ receptor which comprises obtaining total mRNA from the cell using methods well known in the art and contacting the mRNA so obtained with a nucleic acid probe comprising a nucleic acid molecule of at least 15 nucleotides capable of specifically hybridizing with a sequence included within the sequence of a nucleic acid molecule encoding a human 5-$HT_{1F}$ receptor under hybridizing conditions, detecting the presence of mRNA hybridized to the probe, and thereby detecting the expression of the 5-$HT_{1F}$ receptor by the cell. Hybridization of probes to target nucleic acid molecules such as mRNA molecules employs techniques well known in the art. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense olignucleotide having an sequence capable of binding specifically with any sequences of an mRNA molecule which encodes a human 5-$HT_{1F}$ receptor so as to prevent translation of the mRNA molecule. The antisense oligonucleotide may have a sequence capable of binding specifically with any sequences of the cDNA molecule whose sequence is shown in FIG. 1. As used herein, the phrase "binding specifically" means the ability of a nucleic acid sequence to recognize a nucleic acid sequence complementary to its own and to form double-helical segments through hydrogen bonding between complementary base pairs. A particular example of an antisense oligonucleotide is an antisense oligonucleotide comprising chemical analogues of nucleotides.

This invention also provides a pharmaceutical composition comprising an amount of the oligonucleotide described above effective to reduce expression of a human 5-$HT_{1F}$ receptor by passing through a cell membrane and binding specifically with mRNA encoding a human 5-$HT_{1F}$ receptor in the cell so as to prevent its translation and a pharmaceutically acceptable hydrophobic carrier capable of passing through a cell membrane. The oligonucleotide may be coupled to a substance which inactivates mRNA, such as a ribozyme. The pharmaceutically acceptable hydrophobic carrier capable of passing through cell membranes may also comprise a structure which binds to a receptor specific for a selected cell type and is thereby taken up by cells of the selected cell type. The structure may be part of a protein known to bind a cell-type specific receptor, for example an insulin molecule, which would target pancreatic cells. DNA molecules having coding sequences substantially the same as the coding sequence shown in FIG. 1 may be used as the oligonucleotides of the pharmaceutical composition.

This invention also provides a method of treating abnormalities which are alleviated by reduction of expression of a 5-$HT_{1F}$ receptor which comprises administering to a subject an amount of the pharmaceutical composition described above effective to reduce expression of the 5-$HT_{1F}$ receptor by the subject. This invention further provides a method of treating an abnormal condition related to 5-$HT_{1F}$ receptor activity which comprises administering to a subject an amount of the pharmaceutical composition described above effective to reduce expression of the 5-$HT_{1F}$ receptor by the subject. Several examples of such abnormal conditions are dementia, Parkinson's disease, feeding disorders, pathological anxiety, schizophrenia, or a migraine headache.

Antisense oligonucleotide drugs inhibit translation of mRNA encoding these receptors. Synthetic oligonucleotides, or other antisense chemical structures are designed to bind to mRNA encoding the 5-$HT_{1F}$ receptor and inhibit translation of mRNA and are useful as drugs to inhibit expression of 5-$HT_{1F}$ receptor genes in patients. This invention provides a means to therapeutically alter levels of expression of human 5-$HT_{1F}$ receptors by the use of a synthetic antisense oligonucleotide drug (SAOD) which inhibits translation of mRNA encoding these receptors. Synthetic oligonucleotides, or other antisense chemical structures designed to recognize and selectively bind to mRNA, are constructed to be complementary to portions of the nucleotide sequences shown in FIG. 1 of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which binds and takes up the SAOD only within certain selected cell populations. For example, the SAOD may be designed to bind to a receptor found only in a certain cell type, as discussed above. The SAOD is also designed to recognize and selectively bind to the target mRNA sequence, which may correspond to a sequence contained within the sequence shown in FIG. 1 by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10, 435 (1989); H. M. Weintraub, Sci. Am. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce receptor expression in particular target cells of a patient, in any clinical condition which may benefit from reduced expression of $5\text{-}HT_{1F}$ receptors.

This invention provides an antibody directed to the human $5\text{-}HT_{1F}$ receptor, for example a monoclonal antibody directed to an epitope of a human $5\text{-}HT_{1F}$ receptor present on the surface of a cell and having an amino acid sequence substantially the same as an amino acid sequence for a cell surface epitope of the human $5\text{-}HT_{1F}$ receptor included in the amino acid sequence shown in FIG. 1 (Seq. I.D. Nos. 2, 7). Amino acid sequences may be analyzed by methods well known in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIG. 1 will bind to a surface epitope of a human $5\text{-}HT_{1F}$ receptor, as described. Antibodies directed to human $5\text{-}HT_{1F}$ receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk⁻ cells may be used as immunogens to raise such an antibody. Alternatively, synthetic peptides may be prepared using commercially available machines and the amino acid sequence shown in FIG. 1. As a still further alternative, DNA, such as a cDNA or a fragment thereof, may be cloned and expressed and the resulting polypeptide recovered and used as an immunogen. These antibodies are useful to detect the presence of human $5\text{-}HT_{1F}$ receptors encoded by the isolated DNA, or to inhibit the function of the receptors in living animals, in humans, or in biological tissues or fluids isolated from animals or humans.

This invention provides a pharmaceutical composition which comprises an amount of an antibody directed to the human $5\text{-}HT_{1F}$ receptor effective to block binding of naturally occurring ligands to the $5\text{-}HT_{1F}$ receptor, and a pharmaceutically acceptable carrier. A monoclonal antibody directed to an epitope of a human $5\text{-}HT_{1F}$ receptor present on the surface of a cell and having an amino acid sequence substantially the same as an amino acid sequence for a cell surface epitope of the human $5\text{-}HT_{1F}$ receptor included in the amino acid sequence shown in FIG. 1 is useful for this purpose.

This invention also provides a method of treating abnormalities which are alleviated by reduction of expression of a human $5\text{-}HT_{1F}$ receptor which comprises administering to a subject an amount of the pharmaceutical composition described above effective to block binding of naturally occurring ligands to the $5\text{-}HT_{1F}$ receptor and thereby alleviate abnormalities resulting from overexpression of a human $5\text{-}HT_{1F}$ receptor. Binding of the antibody to the receptor prevents the receptor from functioning, thereby neutralizing the effects of overexpression. The monoclonal antibodies described above are both useful for this purpose. This invention additionally provides a method of treating an abnormal condition related to an excess of $5\text{-}HT_{1F}$ receptor activity which comprises administering to a subject an amount of the pharmaceutical composition described above effective to block binding of naturally occurring ligands to the $5\text{-}HT_{1F}$ receptor and thereby alleviate the abnormal condition. Some examples of abnormal conditions are dementia, Parkinson's disease, feeding disorders, pathological anxiety, schizophrenia, and a migraine headache.

This invention provides a method of detecting the presence of a $5\text{-}HT_{1F}$ receptor on the surface of a cell which comprises contacting the cell with an antibody directed to the human $5\text{-}HT_{1F}$ receptor, under conditions permitting binding of the antibody to the receptor, detecting the presence of the antibody bound to the cell, and thereby the presence of the human $5\text{-}HT_{1F}$ receptor on the surface of the cell. Such a method is useful for determining whether a given cell is defective in expression of $5\text{-}HT_{1F}$ receptors on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a human $5\text{-}HT_{1F}$ receptor. This invention also provides a transgenic nonhuman mammal expressing DNA encoding a human $5\text{-}HT_{1F}$ receptor so mutated as to be incapable of normal receptor activity, and not expressing native $5\text{-}HT_{1F}$ receptor. This invention also provides a transgenic nonhuman mammal whose genome comprises antisense DNA complementary to DNA encoding a human $5\text{-}HT_{1F}$ receptor so placed as to be transcribed into antisense mRNA which is complementary to mRNA encoding a $5\text{-}HT_{1F}$ receptor and which hybridizes to mRNA encoding a $5\text{-}HT_{1F}$ receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in FIG. 1 (Seq. I.D. No. 1). An example of a transgenic animal is a transgenic mouse. Examples of tissue specificity-determining regions are the metallothionein promotor (Low, M. J., Lechan, R. M., Hammer, R. E. et al. Science 231:1002–1004 (1986)) and the L7 promotor (Oberdick, J., Smeyne, R. J., Mann, J. R., Jackson, S. and Morgan, J. I. Science 248:223–226 (1990)).

Animal model systems which elucidate the physiological and behavioral roles of human $5\text{-}HT_{1F}$ receptors are produced by creating transgenic animals in which the expression of a $5\text{-}HT_{1F}$ receptor is either increased or decreased, or the amino acid sequence of the expressed $5\text{-}HT_{1F}$ receptor protein is altered, by a variety of techniques. Examples of these techniques include: 1) Insertion of normal or mutant versions of DNA encoding a human $5\text{-}HT_{1F}$ receptor or homologous animal versions of these genes, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)). 2) Homologous recombination (Capecchi M. R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these $5\text{-}HT_{1F}$ receptors. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a human $5\text{-}HT_{1F}$ receptor is purified from a vector (such as plasmid pMO5-hl16a described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against these $5\text{-}HT_{1F}$ receptors even before such drugs become available. These animal model systems are useful for predicting or evaluating possible therapeutic applications of drugs which activate or inhibit these $5\text{-}HT_{1F}$ receptors by inducing or inhibiting expression of the native or trans-gene and thus increasing or decreasing expression of normal or mutant $5\text{-}HT_{1F}$ receptors in the living animal. Thus, a model system is produced in which the biological activity of drugs directed against these $5\text{-}HT_{1F}$ receptors are evaluated before such drugs become available. The transgenic animals which over or under produce the $5\text{-}HT_{1F}$ receptor indicate by their physiological state whether over or under production of the $5\text{-}HT_{1F}$ receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which down-regulates or acts as an antagonist to $5\text{-}HT_{1F}$ receptor is indicated as worth developing, and if a promising therapeutic application is uncovered by these animal model systems, activation or inhibition of the $5\text{-}HT_{1F}$ receptor is achieved therapeutically either by producing agonist or antagonist drugs directed against these $5\text{-}HT_{1F}$ receptors or by any method which increases or decreases the expression of these $5\text{-}HT_{1F}$ receptors in man.

This invention provides a method of determining the physiological effects of expressing varying levels of human $5\text{-}HT_{1F}$ receptors which comprises producing a transgenic nonhuman animal whose levels of human $5\text{-}HT_{1F}$ receptor expression are varied by use of an inducible promoter which regulates human $5\text{-}HT_{1F}$ receptor expression. This invention also provides a method of determining the physiological effects of expressing varying levels of human $5\text{-}HT_{1F}$ receptors which comprises producing a panel of transgenic nonhuman animals each expressing a different amount of human $5\text{-}HT_{1F}$ receptor. Such animals may be produced by introducing different amounts of DNA encoding a human $5\text{-}HT_{1F}$ receptor into the oocytes from which the transgenic animals are developed.

This invention also provides a method for identifying a substance capable of alleviating abnormalities resulting from overexpression of a human $5\text{-}HT_{1F}$ receptor comprising administering the substance to a transgenic nonhuman mammal expressing at least one artificially introduced DNA molecule encoding a human $5\text{-}HT_{1F}$ receptor and determining whether the substance alleviates the physical and behavioral abnormalities displayed by the transgenic nonhuman mammal as a result of overexpression of a human $5\text{-}HT_{1F}$ receptor. As used herein, the term "substance" means a compound or composition which may be natural, synthetic, or a product derived from screening. Examples of DNA molecules are DNA or cDNA molecules having a coding sequence substantially the same as the coding sequence shown in FIG. 1.

This invention provides a pharmaceutical composition comprising an amount of the substance described supra effective to alleviate the abnormalities resulting from overexpression of $5\text{-}HT_{1F}$ receptor and a pharmaceutically acceptable carrier.

This invention further provides a method for treating the abnormalities resulting from overexpression of a human $5\text{-}HT_{1F}$ receptor which comprises administering to a subject an amount of the pharmaceutical composition described above effective to alleviate the abnormalities resulting from overexpression of a human $5\text{-}HT_{1F}$ receptor.

This invention provides a method for identifying a substance capable of alleviating the abnormalities resulting from underexpression of a human $5\text{-}HT_{1F}$ receptor comprising administering the substance to the transgenic nonhuman mammal described above which expresses only nonfunctional human $5\text{-}HT_{1F}$ receptor and determining whether the substance alleviates the physical and behavioral abnormalities displayed by the transgenic nonhuman mammal as a result of underexpression of a human $5\text{-}HT_{1F}$ receptor.

This invention also provides a pharmaceutical composition comprising an amount of a substance effective to alleviate abnormalities resulting from underexpression of 5-HT$_{1F}$ receptor and a pharmaceutically acceptable carrier.

This invention further provides a method for treating the abnormalities resulting from underexpression of a human 5-HT$_{1F}$ receptor which comprises administering to a subject an amount of the pharmaceutical composition described above effective to alleviate the abnormalities resulting from underexpression of a human 5-HT$_{1F}$ receptor.

This invention provides a method for diagnosing a predisposition to a disorder associated with the expression of a specific human 5-HT$_{1F}$ receptor allele which comprises: a) obtaining DNA of subjects suffering from the disorder; b) performing a restriction digest of the DNA with a panel of restriction enzymes; c.electrophoretically separating the resulting DNA fragments on a sizing gel; d) contacting the resulting gel with a nucleic acid probe capable of specifically hybridizing to DNA encoding a human 5-HT$_{1F}$ receptor and labelled with a detectable marker; e) detecting labelled bands which have hydridized to the DNA encoding a human 5-HT$_{1F}$ receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human 5-HT$_{1F}$ receptor allele.

This invention provides a method of preparing the isolated 5-HT$_{1F}$ receptor which comprises inducing cells to express 5-HT$_{1F}$ receptor, recovering the receptor from the resulting cells, and purifying the receptor so recovered. An example of an isolated 5-HT$_{1F}$ receptor is an isolated protein having substantially the same amino acid sequence as the amino acid sequence shown in FIG. 1 (Seq. I.D. Nos. 2, 7). For example, cells can be induced to express receptors by exposure to substances such as hormones. The cells can then be homogenized and the receptor isolated from the homogenate using an affinity column comprising, for example, serotonin or another substance which is known to bind to the receptor. The resulting fractions can then be purified by contacting them with an ion exchange column, and determining which fraction contains receptor activity or binds anti-receptor antibodies.

This invention provides a method of preparing the isolated 5-HT$_{1F}$ receptor which comprises inserting nucleic acid encoding 5-HT$_{1F}$ receptor in a suitable vector, inserting the resulting vector in a suitable host cell, recovering the receptor produced by the resulting cell, and purifying the receptor so recovered. An example of an isolated 5-HT$_{1F}$ receptor is an isolated protein having substantially the same amino acid sequence as the amino acid sequence shown in FIG. 1. This method for preparing 5-HT$_{1F}$ receptor uses recombinant DNA technology methods well known in the art. For example, isolated nucleic acid encoding 5-HT$_{1F}$ receptor is inserted in a suitable vector, such as an expression vector. A suitable host cell, such as a bacterial cell, or a eukaryotic cell such as a yeast cell, is transfected with the vector. 5-HT$_{1F}$ receptor is isolated from the culture medium by affinity purification or by chromatography or by other methods well known in the art.

This invention provides an antisense oligonucleotide having a sequence capable of binding specifically with any sequences of an mRNA molecule which encodes a receptor so as to prevent translation of the mRNA molecule (Seq. I.D. No. 9).

This invention also provides a transgenic nonhuman mammal expressing DNA encoding a receptor.

This invention further provides a transgenic nonhuman mammal expressing DNA encoding a receptor so mutated as to be incapable of normal receptor activity, and not expressing native receptor.

This invention provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

Applicants have identified individual receptor subtype proteins and have described methods for the identification of pharmacological compounds for therapeutic treatments. Pharmacological compounds which are directed against specific receptor subtypes provide effective new therapies with minimal side effects.

This invention identifies for the first time a new receptor protein, its amino acid sequence, and its human gene. Furthermore, this invention describes a previously unrecognized group of receptors within the definition of a 5-HT$_{1F}$ receptor. The information and experimental tools provided by this discovery are useful to generate new therapeutic agents, and new therapeutic or diagnostic assays for this new receptor protein, its associated mRNA molecule or its associated genomic DNA. The information and experimental tools provided by this discovery will be useful to generate new therapeutic agents, and new therapeutic or diagnostic assays for this new receptor protein, its associated mRNA molecule, or its associated genomic DNA.

Specifically, this invention relates to the first isolated of a human cDNA and genomic clone encoding a 5-HT$_{1F}$ receptor. A new human gene for the receptor identified herein as 5-HT$_{1F}$ has been identified and characterized, and a series of related cDNA and genomic clones have been isolated. In addition, the human 5-HT$_{1F}$ receptor has been expressed in Ltk$^-$ cells and NIH3T3 cells by transfecting the cells with the plasmid pMO5-hl16a. The pharmacological binding properties of the protein encoded have been determined, and these binding properties classify this protein as a serotonin 5-HT$_{1F}$ receptor. Mammalian cell lines expressing this human 5-HT$_{1F}$ receptor at the cell surface have been constructed, thus establishing the first well-defined, cultured cell lines with which to study this 5-HT$_{1F}$ receptor.

The invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Materials and Methods

Polymerase Chain Reaction (PCR): The third (III) and fifth (V) transmembrane domains of the following receptors were aligned and used to synthesize a pair of "degenerate" primers: 5-$HT_{1A}$ (Seq. I.D. No. 3), 5-$HT_{1C}$ (Seq. I.D. No. 4), 5-$HT_2$ (Seq. I.D. No. 8) and the 5-$HT_{1D\alpha/\beta}$ (Seq. I.D. Nos. 5 and 6, respectively) receptors (patent pending). These primers hybridize to opposite strands of target sequences to allow amplification of the region between the corresponding transmembrane domains. That primer which was designed to anneal to transmembrane domain III is designated 3.17 and consists of a mixture of 192 different 31-mers with two inosine nucleotides; the primer which annealed to transmembrane domain V is designated 5.5 and consists of a mixture of 288 different 27-mers with five inosine nucleotides. EcoRI linkers were included at the 5' end of primer 3.17, to facilitate the subcloning of the amplified cDNA in pBluescript (Stratagene) vectors. 5 μg of poly (A+) RNA from rat brain was reverse transcribed by avian myeloblastosis virus reverse transcriptase (AMV) including 3 μM each of 3.17 and 5.5 primers. The resulting single-stranded cDNA was used in a PCR reaction under the following conditions: 94° C. for 1 minute, 50° C. for 2 minutes and 72° C. for 3 minutes for 40 cycles. Following PCR, 90 μl of the reaction was phenol:chloroform extracted and precipitated; 10 μl was visualized on a gel using ethidium bromide staining. After precipitation the sample was treated with T4 DNA polymerase and digested with EcoRl prior to separation on a 1% agarose gel. The DNA fragment was isolated from the gel, kinased and cloned into pBluescript. Recombinant clones were analyzed by sequencing.

Cloning and Sequencing: A human lymphocyte genomic library (Stratagene) was screened using the rat S51 fragment (obtained by PCR) as a probe. The probe was labeled with $^{32}P$ by the method of random priming (Feinberg et al., 1983). Hybridization was performed at 50° C. in a solution containing 50% formamide, 10% dextran sulfate, 5×SSC (1×SSC is 0.15 M sodium chloride, 0.015 M sodium citrate), 1×Denhardt's (0.02% polyvinylpyrrolidone, 0.02% Ficoll, and 0.02% bovine serum albumin), and 200 μg/ml of sonicated salmon sperm DNA. The filters were washed at 50° C. in a 0.1×SSC containing 0.1% sodium dodecyl sulfate (SDS) and exposed at −70° C. to Kodak XAR film in the presence of an intensifying screen. Lambda phage hybridizing to the probe were plaque purified and DNA was prepared for Southern blot analysis (Southern, 1975; Maniatis et al., 1982). For subcloning and further Southern blot analysis DNA was inserted into pUC18 (Pharmacia, Piscataway, N.J.). Nucleotide sequence analysis was done by the Sanger dideoxy nucleotide chain-termination method (Sanger 1977) on denatured double-stranded plasmid templates using Sequenase (U.S. Biochemical Corp. Cleveland, Ohio).

Expression: The entire coding region of clone hl16a was cloned into the eukaryotic expression vector pcEXV-3 (Miller, 1986). Stable cell lines were obtained by cotransfection with the plasmid pcEXV-3 (containing the 5-$HT_{1F}$ receptor gene) and the plasmid pGCcos3neo (containing the aminoglycoside transferase gene) into Ltk⁻ cells or NIH3T3 cells using calcium phosphate (reagents obtained from Specialty Media, Lavellette, N.J.). The cells were grown in a controlled environment (37° C. 5% $CO_2$) an monolayers in Dulbecco's modified Eagle medium (Gibco, Grand Island, N.Y.) containing 25 mM glucose and supplemented with 10% bovine calf serum, 100 U/ml penicillin G and 100 μg/ml streptomycin sulfate. Stable clones were then selected for resistance to the antibiotic G-418 and harvested membranes were screened for their ability to bind [$^3H$]serotonin.

Membrane Preparation: Membranes were prepared from transfected Ltk⁻ cells which were grown to 100% confluency. The cells were washed twice with phosphate-buffered saline, scraped from the culture dishes into 5 ml of ice-cold phosphate-buffered saline, and centrifuged at 200×g for 5 min at 4°. The pellet was resuspended in 2.5 ml of ice-cold Tris buffer (20 mM Tris-HCl, pH 7.4 at 23°, 5 mM EDTA) and homogenized by a Wheaton tissue grinder. The lysate was subsequently centrifuged at 200×g for 5 min at 4° to pellet large fragments which were discarded. The supernatant was collected and centrifuged at 40,000×g for 20 min at 4°. The pellet resulting from this centrifugation was washed once in ice-cold Tris wash buffer and finally resuspended in a final buffer containing 50 mM Tris-HCl and 0.5 mM EDTA, pH 7.4 at 23°. Membrane preparations were kept on ice and utilized within two hours for the radioligand binding assays. Protein concentrations were determined by the method of Bradford (1976) using bovine serum albumin as the standard.

Radioligand Binding: [$^3H$]5HT binding was performed using slight modifications of the 5-$HT_{1D}$ assay conditions reported by Herrick-Davis and Titeler (1988) with the omission of masking ligands. Radioligand binding studies were achieved at 37° C. in a total volume of 250 μl of buffer (50 mM Tris, 10 mM $MgCl_2$, 0.2 mM EDTA, 10 μM pargyline, 0.1% ascorbate, pH 7.4 at 37° C.) in 96 well microtiter plates. Saturation studies were conducted using [$^3H$]5-HT at 12 different concentrations ranging from 0.5 nM to 100 nM. Displacement studies were performed using 4.5–5.5 nM [$^3H$]5-HT. The binding profile of drugs in competition experiments was accomplished using 10–12 concentrations of compound. Incubation times were 30 min for both saturation and displacement studies based upon initial investigations which determined equilibrium binding conditions. Nonspecific binding was defined in the presence of 10 μM 5HT. Binding was initiated by the addition of 50 μl membrane homogenates (10–20 μg). The reaction was terminated by rapid filtration through presoaked (0.5% polyethyleneimine filters using 48R Cell Brandel Harvester (Gaithersburg, Md.). Subsequently, filters were washed for 5 sec with ice cold buffer (50 mM Tris HCL, pH 7.4 at 4° C.), dried and placed into vials containing 2.5 ml of Readi-Safe (Beckman, Fullerton, Calif.) and radioactivity was measured using a Beckman LS 5000TA liquid scintillation counter. The efficiency of counting of [$^3H$]5HT averaged between 45–50%. Binding data was analyzed by computer-assisted nonlinear regression analysis (Accufit and Accucomp, Lundon Software, Chagrin Falls, Ohio). $IC_{50}$ values were converted to $K_1$ values using the Cheng-Prusoff equation (1973). All experiments were performed in triplicate.

Measurement of cAMP Formation

Transfected NIH3T3 cells (estimated Bmax from one point competition studies=486 fmol/mg of protein) were incubated in DMEM, 5 mM theophylline, 10 mM Hepes (4-[2-Hydroxyethyl]-1-piperazineethanesulfonic acid), 10 μM pargyline, for 20 minutes at 37° C., CO2. Drug dose-effect curves were then conducted by adding 6 different final concentrations of drug, followed immediately by the addition of forskolin (10 μM). Subsequently, the cells were incubated for an additional 10 minutes at 37° C., 5% CO2. The media was aspirated and the reaction terminated by the addition of 100 mM HCl. The plates were stored at 4° C. for 15 minutes and centrifuged for 5 minutes (500×g at 4° C.) to pellet cellular debris. Aliquots of the supernatant fraction were then stored at −20° C. prior to assessment of cAMP formation by radioimmunoassay (cAMP Radioimmunoassay kit, Advanced Magnetics, Cambridge, Mass.).

Tissue Localization Studies. Human tissues (NDRI) were homogenized and total RNA extracted (Sambrook et al., 1989). cDNA was prepared from 5 μg of total RNA with random hexanucleotide primers (500 pmoles) using Superscript reverse transcriptase (BRL) in PCR reaction buffer (Cetus Corp.) containing 1 mM dNTPs, at 42° C. for 1 hr. An aliquot of the first strand cDNA was diluted (1:5) in a 50 μl PCR reaction mixture (200 μM dNTPs final concentration) containing 1.25 U of Taq polymerase and 1 μM of primers from the sense strand (5'TCTATTCTGGAGGCACCAAGGAAC3') (SEQ ID NO:10) and from the antisense strand (5'TGTTGATGGGTCAGATAAAGACTT3') (SEQ ID NO:11). The PCR products were run on a 1.5% agarose gel and transferred to charged nylon membrane (2etaProbe, Bio-Rad). Filters were hybridized and washed under high stringency.

In Situ Hybridization. In situ hybridization was performed as described previously (McCabe et al., 1989) using male Hartley guinea pigs (300–350 g). A fragment of the guinea pig 5-HT$_{1F}$ receptor gene was cloned by homology and sequenced. 45-base oligoprobes synthesized to the 4,5 loop and 5' untranslated regions were 3' end-labeled with $^{35}$S-dATP to a specific activity of 4×10$^9$ Ci/mmol. The nucleotide sequences were: 5'GTGATGCTTGATGATGCACT-CATCATCTCGGCTTGTCCCCTGGTG 3' and 5'TAGCAGTTCCTCTGAGGT-CAAGTTTTGATCAGAAGAGTTTAAGAA 3' (SEQ ID NO:13). Sense probes, melting temperature, and RNase pretreatment were used as controls. Sections were exposed to Kodak X-OMAT AR film for 1 week or coated with Kodak NTB-2 emulsion/2% glycerol (1:1) for 2 weeks. Similar experiments were also done on human tissue.

Drugs: [$^3$H]5-HT (specific activity=28 Ci/mmole) was obtained from New England Nuclear, Boston, Mass. All other chemicals were obtained from commercial sources and were of the highest grade known purity available.

Results

Cloning of a Novel Gene Encoding a 5HT$_{1F}$ Receptor

Polyadenylated (poly A−) RNA prepared from rat brain was reverse transcribed and the resulting cDNAs were subjected to amplification by PCR with the use of a set of "degenerate" primers. The synthesis of these primers were based on sequences corresponding to the third and fifth transmembrane segments of the current set of available serotonin receptors. The primers were designed to amplify only serotonin specific sequences. This was accomplished, particularly with the transmembrane domain V primer, which was designed to anneal at its 3' end only to the sequence "AFY(F)IP". We have determined by sequence analysis that the presence of an alanine (A) rather than a serine (S) in the position immediately amino-terminal to the sequence "FY(F)IP" is an amino acid which can distinguish the closely related adrenergic and dopaminergic receptor families from the serotonergic receptor family. After 30 amplification cycles, agarose gel electrophoresis revealed a clear pattern of cDNA species of approximately 250 base pairs. Individual cDNAs were cloned directly into pBluescript and subjected to sequence analysis. One clone, designated S51, was observed to encode a novel serotonin receptor. We then screened a human genomic placental library with the PCR fragment S51. Isolation of the full-length coding region was obtained from a genomic clone designated hl16a.

Nucleotide Sequence and Deduced Amino Acid Sequence of hl16a

DNA sequence information obtained from clone hl16a is shown in FIG. 1. An open reading frame extending from an ATG start codon at position 1 to a stop codon at position 1098 can encode a protein 366 amino acids in length, having a relative molecular mass ($M_r$) of 41,660. A comparison of this protein sequence with previously characterized neurotransmitter receptors indicates that hl16a encodes a receptor which is a new member of a family of molecules which span the lipid bilayer seven times and couple to guanine nucleotide regulatory proteins (the G protein-coupled receptor family). A variety of structural features which are invariant in this family were present including the aspartic acid residues of transmembrane regions II and III, the DRY sequence at the end of transmembrane region III, and the conserved proline residues of transmembrane regions IV, V, VI and VII (Hartig et al. and references therein), were present in clone hl16a. A comparison of the transmembrane homology of hl16a to the other cloned serotonin receptors is shown if FIG. 2 exhibits the following order of identity: 5-HT$_{1D\alpha}$(61%), 5-HT$_{1DS}$ (59%), 5-HT$_{1A}$ (54%), 5-HT$_{1C}$ (44%) and 5-HT$_2$ (44%).

Receptor Expression in Transfected Mammalian Cells

Saturation analysis of membranes prepared from stably transfected Ltk- cells demonstrated that the receptor expressed was saturable and of high affinity. Scratchard plot analysis by non-linear regression revealed a Kd of 9.2±0.99 nM (mean±S.E.M., n=4) and a B$_{max}$ 4.4=0.36 picomoles/mg of protein (mean±S.E.M., n=4). The percent specific binding determined at the measured Kd value for [$^3$H]5-HT was greater than 85% of total binding. Furthermore, evidence that the receptor is coupled to a G-protein was demonstrated by the ability of Gpp(NH)p, a non-hydrolyzable analog of GTP, to inhibit the specific binding of [$^3$H]5-HT (IC$_{50}$= 243±115, n$_H$=0.71±0.08, I$_{max}$=55.6±3.2%; means ±S.E.M., n=3). Additional data demonstrating that this coupling to a G-protein is functionally relevant is provided below.

Pharmacological analysis of the receptor was accomplished by testing the ability of drugs from different chemical classes to displace [3H]5-HT specific binding (Table 1). Of the compounds investigated, 5-HT possessed the highest affinity which according to the classification system of Peroutka and Snyder (1979) makes this site a member of the 5-HT$_1$ class. Interestingly, 5-CT possessed low affinity and, thus, discriminates this receptor from that of the 5-HT$_{1D}$ receptor as well as other members of this class. The one exception appears to be the recently cloned 5-HT$_{1E}$ receptor which also has low affinity for 5-CT (U.S. Ser. No. 803,626, filed Dec. 2, 1991, copending). Various ergoline compounds also bound with high affinity including methylergonovine and methysergide. Excluding 1-napthylpiperazine (K1=54), piperazine derivatives had low affinity. Interestingly, the rauwolfia alkaloids, rauwolscine and yohimbine, which are alpha-2 adrenergic antagonists had fair affinity for this serotonergic receptor. Furthermore, miscellaneous serotonergic agents that possess high affinity for various receptors within the serotonin family including ketanserin (5-HT$_2$), 8-OH-DPAT (5-HT$_{1A}$), DOI (5-HT$_{1C}$/5-HT$_2$), spiperone (5-HT$_{1A}$/5-HT$_2$), pindolol (5-HT$_{1A}$/5-HT$_{1B}$), and zacopride (5-HT$_3$) had very poor affinity. Taken together, the pharmacological profile of the 5-HT$_{1F}$ receptor is unique and contrasts to that of other known serotonin receptors. Interestingly, the agonist rank order of potency (but not antagonist profile) matches one described for large motorneurons in the spinal cord evaluated electrophysiologically (Connel et al., 1989). Accordingly, the probability of developing selective drugs for this receptor subtype is increased. The functional 5-HT response (1 $\mu$M) was completely blocked by the nonselective antagonist methiothepin (10 $\mu$M). This antagonism was surmountable (FIG. 3), indicating probable competitive antagonism. The dose shift produced by methiothepin yielded an apparent K$_D$ of 438±14 nM, consistent with the K$_1$ for this compound (Table 1). No direct effect of methiothepin was observed. No other compound tested in this study was an antagonist. In addition, no evidence for coupling of this receptor to PI turnover was detected at a dose of 10 $\mu$M 5-HT.

TABLE 1

Ki (nM) values of various drugs for the inhibition of [$^3$H]5-HT specific binding to clonal 5-HT$_{1F}$ cell membranes. Binding assays were performed with 4.5–5.5 nM of [$^3$H]5-HT and 10–12 different concentrations of each inhibitory drug. K1 values were calculated from the IC$_{50}$ values using the Cheng-Prusoff equation. Each value is the mean ± S.E.M. of 2–4 independent determinations.

| COMPOUND | K1 (nM) |
| --- | --- |
| 5-HT | 10.3 ± 2.0 |
| Sumatriptan | 23.0 ± 11.0 |
| Ergonovine | 31.0 ± 1.5 |
| Methylergonovine | 31.0 ± 11.0 |
| Methysergide | 34.0 ± 4.9 |
| 5-Methoxy-N,N-DMT | 37.5 ± 1.5 |
| 1-Napthylpiperazine | 54.0 ± 3.8 |
| Yohimbine | 92.0 ± 11.0 |
| Ergotamine | 171 ± 28 |
| α-Methyl-5-HT | 184 ± 35 |
| NAN 190 | 203 ± 13 |
| Dihydroergotamine | 276 ± 49 |
| Metergoline | 341 ± 71 |
| 2-Methyl-5-HT | 413 ± 5.6 |
| Methiothepin | 652 ± 41 |
| 5-CT | 717 ± 71 |
| TFMPP | 1,002 ± 85 |
| 5-MT | 1,116 ± 197 |
| SCH 23390 | 1,492 ± 165 |
| 5-Benzoxytryptamine | 1,495 ± 893 |
| DP-5-CT | 1,613 ± 817 |
| DOI | 1,739 ± 84 |
| 8-OH-DPAT | 1,772 ± 38 |
| 5-Fluorotryptamine | 1,805 ± 220 |
| mCPP | 2,020 ± 36 |
| Tryptamine | 2,409 ± 103 |
| Quipanzine | 4,668 ± 814 |
| Ritanserin | 3,521 ± 86 |
| Propanolol | 8,709 ± 97 |
| Ketanserin | >10,000 |
| Spiperone | >10,000 |
| Zacopride | >10,000 |
| Pindolol | >10,000 |
| Mesulergine | >10,000 |
| Harmaline | >10,000 |
| Melatonin | >10,000 | cAMP Assay

Additional supporting evidence that the 5-HT1F receptor is functionally coupled to a G-protein was obtained by testing the ability of 5-HT as well as other representative serotonergic drugs to inhibit forskolin stimulated cAMP production in NIH3T3 cells transfected with the 5-HT1F receptor. The endogenous indoleamine, 5-HT, produced a concentration-related decrease in forskolin-stimulated cAMP production with an EC50 of 7.1 ±1.3 nM (n=4). The maximum inhibition of cAMP production by 5-HT was 67±5.4%. Additionally, the serotonergic compounds 1-napthylpiperazine and lysergol inhibited forskolin-stimulated cAMP production with EC50 value of 4.5±0.2 nM and 8.8±4.3 nM (n=2), respectively.

Receptor Localization Studies

Figure 5A:
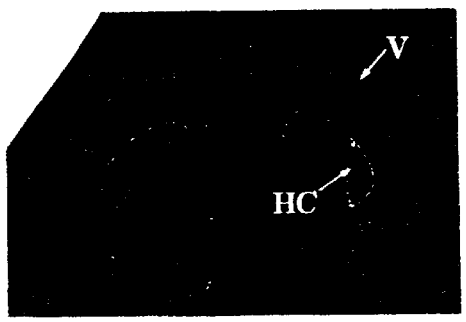
Figure 5B:
Figure 5C:
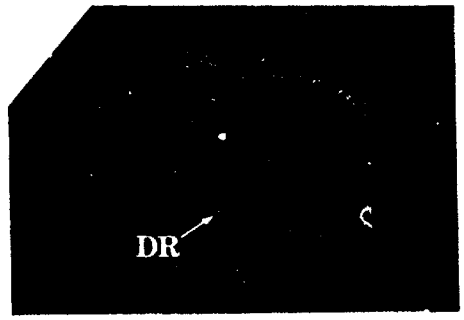
Figure 5D:
Figure 5E:

Expression of the 5-HT$_{1F}$ transcripts was analyzed from PCR-northern blots and in situ hybridization studies. By PCR, we detected 5-HT$_{1F}$ receptor mRNA in the human brain, uterus (endometrium and myometrium) and mesentery (FIG. 4) but not in kidney, liver, spleen, heart, pancreas, or testes. In in situ hybridization experiments, we observed 5-HT$_{1F}$ transcripts in lamina V of frontal cortex (FIG. 5A) in large pyramidal cells (FIG. 5D). Moderate labeling was also detected over layer VI non-pyramidal neurons. In both layer V and layer VI, the labeling was most evident in dorsal sensorimotor neocortex, and in cingulate and retrosplenal cortices (FIG. 5C). The pyramidal cells in the piriform cortex were heavily labeled as were large neurons in the raphe nuclei (FIG. 5E). Hippocampal pyramidal cells in CA1–CA3 were moderately labeled, as were the granule cells in the dentate gyrus, and some neurons in the nucleus of the solitary tract. Little labeling was found in the thalamus and hypothalamus. Significant labelling was also found in the large motoneurons of the ventral horn of the spinal cord. The localization in the human was found to be in good concordance with that observed in the guinea pig.

Discussion

The deduced amino acid sequence of hl16a was analyzed to uncover relationships between it and the other cloned serotonin receptor sequences. Although the homology within the membrane spanning domains was greatest with the 5-HT$_{1D\alpha}$receptor (FIG. 2), the nature of this newly cloned receptor could not be clearly predicted. The rational for this ambiguity is the interpretation of the transmembrane domain homology (approximately 60%) to the 5-HT$_{1D\alpha}$and 5-HT$_{1D\beta}$receptor subfamily. Closely related members of a "subfamily" of serotonin receptors (i.e. "subtypes") generally share a common transmitter and also have similar pharmacological profiles and physiological roles (for example, 5-HT$_2$ and 5-HT$_{1C}$ or 5-HT$_{1D\alpha}$and 5-HT$_{1D\beta}$). Such "subtypes" display an amino acid identity of approximately 75–80% in their transmembrane domains. Serotonin receptors which are not members of the same "subfamily", but are members of the serotonin "family" (in which the receptors use the same neurotransmitter; i.e. 5-HT$_2$ and 5-HT$_{1D\alpha}$) generally show much lower transmembrane homology (approximately 45%). Such transmembrane amino acid homologies can, therefore, give insight into the relationship between receptors and be used as predictors of receptor pharmacology. According to this type of analysis, although the newly cloned receptor appears to be more related to the 5-HT$_{1D}$ subfamily, it is likely to be in a subfamily distinct from all the other serotonin receptors. Interestingly, the transmembrane homology between the 5HT$_{1E}$ (Levy et al., 1992; McAllister et al. 1992; Zgombick et al., 1992) and 5-HT$_{1F}$ (Amlaiky et al., 1992; Adham et al., in press) receptors is 72%. It is therefore possible that these receptors maybe "subtypes", rather than members of distinct "subfamilies".

The present pharmacological evidence substantiates the existence of a novel serotonin receptor in the human brain and peripheral tissues. Comparison of the binding affinities for various drugs observed in native membranes for other known serotonergic receptors (see Hoyer, 1989) to that of the 5-HT$_{1F}$ receptor demonstrates that the pharmacological profile does not fit any known receptor to date. The cloning of the 5-HT$_{1F}$ site will now allow more extensive investigations into the nature of this unique serotonergic receptor.

The structure-activity relationships observed in the present study suggest that there are important requirements for high affinity binding to the 5-HT$_{1F}$ receptor. Substitution or removal of the 5-hydroxy group on serotonin significantly decreases the affinity for the receptor (egs., tryptamine, 5-methoxytryptamine and 5-carboxyamidotryptamine). Additionally, α-methylation and 2-methylation of 5-HT lowers its affinity by 20 and 40 fold, respectively, for the 5-HT$_{1F}$ site. In contrast to these substitutions, N,N-dimethylation of the aliphatic side chain of the indole ring increases the affinity approximately 20 fold (unpublished observations). Interestingly, 5-methoxy-N,N-dimethyltryptamine which possesses both a 5-hydroxy substitution as well as a N,N-dimethylation has an affinity much higher than the other 5-substituted tryptamine derivatives. Basic structural requirements of the ergoline derivatives demonstrate that N-methylation of the indole ring does not decrease affinity as does bulky substitutions. Furthermore, piperazine derivatives are not bound at high affinity.

Notably, the application of the human 5-HT$_{1F}$ receptor clone to pharmaceutical research can lead to new drug design and development. In this regard, it is important to point out that the affinities of sumatriptan, methylergonovine and methysergide for this receptor suggest that this site may be involved in the control of migraine headaches. Certainly, these compounds have had success in the clinic for the treatment of this debilitating disorder (Sleight et al., 1990). Notably, however, it has been thought that the action of these compounds is mediated at 5-HT1D receptors for sumatriptan and 5-HT2 receptors for methysergide. Interestingly, methylergonovine may be an active metabolite of methysergide which can be responsible for some of the therapeutic anti-migraine effects of methysergide. This novel site with affinity for these agents would now suggest that there is one serotonergic receptor which may be responsible for both the pathogenesis and, accordingly, the pharmacological treatment. Importantly, the agents prescribed for migraine are not selective for any one particular serotonin receptor and, thus, the physiological significance of drugs acting at one specific site remains controversial (Humphrey P. P. A. et al., 1990). The notion that the 5-HT$_{1F}$ receptor is involved in migraine may be supported by evidence demonstrating that metergoline which has high affinity for the 5-HT$_{1D}$ receptor does not block the effects of sumatriptan in the dog saphenous vein (Sumner and Humphrey, 1990) inferring that this vascular model may contain the novel 5-HT$_{1F}$ site. Furthermore, this data can support the idea that sumatriptan acts at 5-HT$_{1F}$ receptors as an anti-migraine drug. Localization of transcripts for the 5-HT$_{1F}$ receptor in the spinal trigeminal nucleus by in situ hybridization strongly supports this contention (Buzzi et al.,1990, 1991; Moskowitz et al., 1992). The potential of the 5-HT$_{1F}$ receptor as a novel target for migraine where selective drugs may be developed is an exciting possibility which needs to be explored.

Further insight into potential therapeutic significance of the 5-HT1F receptor has been obtained through localization studies using PCR and in situ hybridization. Localization of transcripts for this receptor indicates a relatively selective tissue distribution. Of tissues reported here, the 5-HT$_{1F}$ receptor was only detected in a few including the brain, uterus, and mesentery. The possible role of this receptor in uterine or vascular function is intriguing. Future studies defining the specific cell type(s) in these tissues which express the receptor may provide insight into its function in the periphery. Possibilities for therapeutic benefit include dysmenorrhea and labor induction uterus) and hypertension (vascular components of mesentery) and obesity (adipose components). In the brain, the expression of the 5-HT1F receptor had a limited distribution compared to that of other serotonin receptors. In the neocortex, labelling of layer V pyramidal neurons may indicate a functional role for the 5-HT$_{1F}$ receptor protein in the integration of sensorimotor (somatodendritic; frontal cortex) or afferent information associated with limbic functions (somatodendritic; cingulate/retrosplenial cortex), or in spinal cord processes (axonal). Intense labeling was detected in the large motoneurons of the ventral horn of the spinal cord. Strong labeling was also detected in hippocampal pyramidal cells, in several thalamic nuclei, and in the dorsal raphe. The detection of transcripts for this gene in the dorsal raphe nucleus indicates a possible role as an autoreceptor. Autoreceptor function opens the possibility that the 5-HT$_{1F}$ receptor could be involved in any or all of the known actions of serotonin including therapeutic potential in anxiety, depression, sleep disorders including jet lag, appetite control, sexual dysfunction, gastrointestinal motility including irritable bowel disease, and cardiovascular regulation. In addition, localization to the large motoneurons indicates a possible role in spasticity and other disorders of movement.

Another consideration for therapeutic application of this site may be related to the treatment of feeding disorders such as obesity, bulimea nervosa and/or anorexia nervosa. The involvement of serotonin and feeding behavior has received much attention during the last decade. It is now known that many of the identified and well-characterized serotonergic receptors are capable of modulating feeding (Blundell and Lawton, 1990). Notably, serotonin uptake blockers which have been used to treat feeding disorders act nonselectively and as such have side-effect potential (Jimerson et al., 1990). The fact that the 5-HT$_{1F}$ receptor has been cloned from both peripheral and central sites, and has been localized by both PCR and by in situ hybridization, suggests from an anatomical standpoint that it can be found in strategic locations where feeding may be altered. Although many different serotonergic receptors are involved in feeding, the search for the one site that can be exploited for selective drug development has yet to be found. There is no doubt that interest exists in finding drugs that interact with the serotonin system for the treatment of feeding disorders (Cooper, 1989).

Overall, the 5-HT$_{1F}$ receptor can be an important site stimulated by nonselectively blocking serotonin uptake as is accomplished with certain antidepressants. In regard to this, serotonin uptake blockers are effective in treating neuropsychiatric disorders such as depression and obsessive-compulsive illness (Asberg et al., 1986; Sleight et al., 1990; Insel et al., 1985). However, these agents have side effects and, in fact, the mechanism of action for these compounds are not linked to any particular serotonergic receptor. The possibility that agents selective for the 5-HT$_{1F}$ receptor may have clinical utility as antidepressants, for example, without the side effects attributed to current treatment modalities can have significant implications for drug therapy. The localization of the 5-HT1F receptor in the raphe nuclei, and therefore its potential role as an autoreceptor, further supports the role for this receptor subtype in depression.

In summary, the pharmacological profile of the cloned human 5-HT$_{1F}$ receptor is unique and contrasts to other known serotonergic receptors. The utility of this site expressed in a cellular system and, thus, isolated for study will create excellent opportunities in drug development directed towards a novel serotonergic receptor that may have wide-range implications for drug therapy. Ultimately, indepth investigations into the localization of this receptor in brain and peripheral tissue will target new sites that may lead to functional roles of the serotonergic receptor. Indeed, the potential therapeutic applications may extend to neuropsychiatric disorders including depression, anxiety, schizophrenia, dementia and obsessive-compulsive illness as well as obesity and migraine.

Additionally, the localization of the 5-HT$_{1F}$ receptor in the spinal cord suggests possible roles for this subtype ion analgesia as well as spasticity. The clear evidence of involvement of this receptor in the ventral horn further supports the possible role in motor control. Interestingly, the agonist profile of the 5-HT$_{1F}$ receptor matches that reported for large motoneurons of the spinal cord measured electrophysiologically (Connel et al., 1989). In addition, the presence of the 5-HT$_{1F}$ receptor in the mesentery, at major resistance bed of the vascular tree, indicated a role in the control of blood pressure. A detailed accounting of the localization and therapeutic potential is presented in Table II.

TABLE II

Summary of the localization of mRNA for the 5-HT$_{1F}$ receptor in the guinea pig and human CNS. Experiments were performed as described (methods). Each experiment was replicated 2–3 times. Potential therapeutic roles anticipated base or these data are indicated.

LOCALIZATION OF HUMAN 5HT$_{1F}$ mRNA*

| AREAS | PROJECTIONS | THERAPEUTIC RELEVANCE |
|---|---|---|
| FRONTAL CORTEX | Main projections to striatum, dorsal thalamus, and superior colliculus. | Potential application for the development of treatments for schizophrenia and mood disorders. |
| CAUDATE NUCLEUS | Primary projections to globus pallidus, substantia nigra. | Potential treatment of any basal ganglia disorder, including Parkinson's disease, Huntington's chorea, or tardive dyskinesia. |
| HIPPOCAMPAL FORMATION | Pyramidal neurons project mainly within the hippocampus, and also to the septum. | Primary locus for treatment of memory disorders, e.g. Alzheimer's disease or for cognitive enhancement in people with learning disabilities. Also possible treatment for temporal lobe epilepsy. |
| AMYGDALA | Cells in amygdala have widespread projections to cortex, hippocampus, basal ganglia, hypothalamus, and brainstem autonomic centers. | Wide range of potential applications. These include treatment of autonomic dysfunctions such as cardiac arrhythmias and non-adaptive response to environmental stressors. Also potential treatment of mood disorders, such as bipolar syndrome. |
| HYPOGLOSSAL NUCLEUS | Main projections to somatic skeletal musculature of the tongue. | Treatment of verbal apraxia. |
| DORSAL EFFERENT NUCLEUS OF THE VAGUS | Principal projections are to the parasympathetic ganglia and abdominal viscera. | May have some application to the treatment of stress-related ulcers and iritable bowel disease. |
| NUCLEUS OF THE SOLITARY TRACT | Main projections are to thalamus, amygdala, rostroventral medulla, and the Al noradrenergic cell group of the dorsal medulla. | Varied potential applications, with regulation of cardiovascular function the most prominent, e.g. an anti-hypertensive. |
| GRACILE NUCLEUS | Provides innervation of lumbosacral spinal cord. | Potential applications for the treatment of dermatitis, or pain associated with itching. |
| CUNEATE NUCLEUS | Provides innervation of cervical spinal cord. | Potential applications for the treatment of dermatitis, or pain associated with itching. |
| SPINAL TRIGEMINAL NUCLEUS | Main projections are to the contralateral ventrobasal thalamus, the posterior thalamic n., the zona incerta, the superior colliculus, and the motor nuclei of trigeminal. | Potential treatment of migraine headaches, and other pain syndromes such as trigeminal neuralgia. |
| OLIVARY COMPLEX | Primary projections are to the cerebellum. | Treatment of ataxia associated with olivopontocerebellar atrophy, or tremors accompanying some neurodegenerative diseases |

TABLE II-continued

Summary of the localization of mRNA for the 5-HT$_{1F}$ receptor in the guinea pig and human CNS. Experiments were performed as described (methods). Each experiment was replicated 2–3 times. Potential therapeutic roles anticipated base or these data are indicated.

LOCALIZATION OF HUMAN 5HT$_{1F}$ mRNA*

| AREAS | PROJECTIONS | THERAPEUTIC RELEVANCE |
|---|---|---|
| RETICULAR FORMATION | Projections to the intra-laminar and dorsomedial n. of thalamus, the hypothalamus, supramammillary and lateral mammillary nuclei, theseptum, the diagonal band, spinal cord, cerebellum, brainstem autonomic nuclei. | Involvement in cardiac pressor and depressor responses suggests a role in blood pressure regulation and possibly a treatment for hypertension. Also possible application for the treatment of urinary retention disorders, and in the management of pain. |
| MEDIAL VESTIBULAR NUCLEUS | Projections to oculomotor complex and cervical spinal cord motor neurons. | Treatment of motion sickness. |
| CEREBELLAR PURKINJE CELLS | Projections only to deep cerebellar nuclei. | Potential treatment of movement disorders, particularly those involving planned movements, or those involving abnormalities of gait or stance. |
| SPINAL CORD VENTRAL HORN | Ascending dorsal horn projections to thalamus, brainstem reticular formation and central gray. Ventral horn projections to skeletal and/or smooth muscle. | Primary site for treatment of pain, and for possible anesthetic applications. Also possible therapies for spasticity and movement disorders. |
| ANTERIOR OLFACTORY NUCLEI and PIRIFORM CORTEX | Widespread projections to brain olfactory centers, to limbic system, hypothalamus, thalamus, and striatum. | Treatment of olfactory disorders (dysosmais) associated with many neurological syndromes. |
| LAYER V of NEOCORTEX | Cells of layer V project primarily to other cortical areas, and to basal ganglia. | Enhancement of memory for motor tasks, particularly in certain amnestic syndromes, e.g. Alzheimer's disease. |
| CAUDATE-PUTAMEN and NUCLEUS ACCUMBENS | Medium spiny neurons project to globus pallidus, entopeduncular n., and substantia nigra. | Potential treatment of any basal ganglia disorder, including Parkinson's disease, Huntington's chorea, or tardive dyskinesia. |
| AMYGDALA | Cells in amygdala have widespread projections to cortex, hippocampus, basal ganglia, hypothalamus, and brainstem autonomic centers. | Wide range of potential applications. These include treatment of autonomic dysfunctions such as cardiac arrhythmias and non-adaptive response to environmental stressors. Also potential treatment of mood disorders, such as bipolar syndrome. |
| HIPPOCAMPUS | Pyramidal neurons project mainly within the hippocampus, and also to the septum. | Primary locus for treatment of memory disorders, e.g. Alzheimer's disease or for cognitive enhancement in people with learning disabilities. Also possible treatment for temporal lobe epilepsy. |
| DORSAL RAPHE | Extensive projections to cerebral cortex, frontal striatum, limbic structures, olfactory tubercle, central gray, hippocampus, and spinal cord. | Treatment of pain syndromes, including migraine headache. Involvement of raphe in general arousal/attentional processes makes this a possible target for treatment of attentional dysfunctions, such as those observed in Alzheimer's disease, or in developmental disabilities. Potential application in the treatment of depression. |
| PONTINE NUCLEI | Major projection is to the cerebellar cortex. | Potential treatment of movement disorders, particularly planned movement, and gait disorders such as Friedrich's ataxia. |
| INFERIOR COLLICULUS | Major obligatory synaptic station in ascending auditory pathway. | |
| TRIGEMINAL NUCLEAR COMPLEX | Main projections are to the contralateral ventrobasal thalamus, the posterior thalamic n., the zona incerta, the superior colliculus, and the motor nuclei of trigeminal. | Potential treatment of migraine headaches, and other pain syndromes such as trigeminal neuralgia. |

TABLE II-continued

Summary of the localization of mRNA for the 5-HT$_{1F}$ receptor in the guinea pig and human CNS. Experiments were performed as described (methods). Each experiment was replicated 2–3 times. Potential therapeutic roles anticipated base or these data are indicated.

LOCALIZATION OF HUMAN 5HT$_{1E}$ mRNA*

| AREAS | PROJECTIONS | THERAPEUTIC RELEVANCE |
|---|---|---|
| PONTINE RETICULAR FORMATION A. GIGANTOCELLULAR RETICULAR NUCLEUS B. PARAGIGANTOCELLULAR RETICULAR NUCLEUS C. RAPHE MAGNUS | Projections to the intra-laminar and dorsomedial n. of thalamus, the hypothalamus, supramammillary and lateral mammillary nuclei, the septum, the diagonal band, spinal cord, cerebellum, brainstem autonomic nuclei | Involvement in cardiac pressor and depressor responses suggests a role in blood pressure regulation and possibly a treatment for hypertension. Also possible application for the treatment of urinary retention disorders, and in the management of pain. |
| MEDIAL VESTIBULAR NUCLEUS | Projections to oculomotor complex and cervical spinal cord motor neurons. | Treatment of motion sickness. |
| CEREBELLAR PURKINJE CELLS | Projections only to deep cerebellar nuclei. | Potential treatment of movement disorders, particularly those involving planned movements, or those involving abnormalities of gait or stance. |
| SPINAL CORD | Ascending dorsal horn projections to thalamus, brainstem reticular formation and central gray. Ventral horn projections to skeletal and/or smooth muscle. | Primary site for treatment of pain, and for possible anesthetic applications. Also possible therapies for spasticity and movement disorders. |

References

Adham, N., Kao, H–T., Schechter, L. E., Bard, J., Olsen, M., Urquhart, D., Durkin, M., Hartig, P. R., Weinshank R. L., and Branchek, T. A. Cloning of Another Human Serotonin Receptor (5-HT$_{1F}$): A fifth 5-Ht$_1$ Receptor Subtype Coupled to the Inhibition of Adenylate Cyclase. Proc. Natl. Acad. Sci., U.S.A., in press.

Amlaiky, N., Ramboz, S., Boschert, U., Plassat, J–L. and Hen, R.: Isolation of a mouse "5HT1E-like" serotonin receptor expressed predominantly in hippocampus. J. Biol. Chem. 267:19761–19764, 1992.

Asberg, M., Eriksson, B., Matensson, B., Traskman-Bendz, L. and Wagner, A.: Therapeutic effects of serotonin uptake inhibitors in depression. J. Clin. Psychiat. 47:23–35, 1986.

Blundell, J. E. and Lawton, C. L.: Serotonin receptor subtypes and the organisation of feeding behaviour: Experimental models. In: Serotonin: From cell biology to pharmacology and therapeutics. (eds. Paoletti, R., Vanhoutte, P. M., Brunello, N. and Maggi, F. M.) Boston:Kluwer Academic Publishers, pp 213–219, 1990.

Bradford, M.: A rapid and sensitive method for the quantification of microgram quantities of protein utilizing the principle of protein-dye binding. Anal. Biochem. 72:248–254, 1976.

Branchek, T., Weinshank, R. L., Macchi, M. J., Zgombick, J. M. and Hartig, P. R.: Cloning and expression of a human 5HT1D receptor. The Second IUPHAR Satellite Meeting on Serotonin, Basel, Switzerland, Jul. 11–13, 1990, Abstract #2.

Buzzi, M. G. and Moskowitz, M. A.: the antimigraine drug, sumatriptan (GR43175), selectively blocks neurogenic plasma extravasation from blood vessels in dura mater. Br. J. Pharmacol. 99:202–206, 1990.

Buzzi, M. G., Moskowitz, M. A., Peroutka, S. J. and Byun, B.: Further characterization of the putative 5-HT receptor which mediates blockade of neurogenic plasma extravasation in rat dura mater. Br. J.Pharmacol. 103:1421–1428, 1991.

Cheng, Y. C. and Prusoff, W. H.: Relationship between the inhibition constant (Ki) and the concentration of inhibitor which causes 50% inhibition (IC50) of an enzyme reaction. Biochem. Pharmacol. 22:3099–3108, 1973.

Connel, L. A. and Wallis, D. I.: 5-hydroxytryptamine depolarizes neonatal rat motorneurones through a receptor unrelated to an identified binding site. Neuropharmacology 28:625–635, 1989.

Cooper, S. J.: Drugs interacting with 5-HT systems show promise for treatment of eating disorders. TIPS 10:56–57, 1989.

Fargin, A., Raymond, J. R., Lohse, M. J., Kobilka, B. K. Caron, M. G. and Lefkowitz, R. J.: The genomic clone G-21 which resembles a β-adrenergic receptor sequence encodes the 5-HT1A receptor. Nature 335:358–360, 1988.

Feinberg, A. P., and Vogelstein, B. A technique for radiolabeling DNA restriction endonuclease fragments to high specific activity. Anal.Biochem. 132:6–13, 1983.

Gaddum, J. H. and Picarelli, Z. P.: Two kinds of tryptamine receptor. Brit. J. Pharmacol. 12:323–328, 1957.

Glennon, R. A.: Serotonin receptors: Clinical implications. Neurosci. Biobehav. Rev. 14:35–47, 1990.

Green, A. R.: Neuropharmacology of serotonin. Oxford: Oxford University Press, 1985.

Hamon, M., Lanfumey, L., El Mestikawy, S., Boni, C., Miquel, M.-C., Bolanos, F., Schechter, L. and Gozlan, H.: The main features of central 5-HT1 receptors. Neuropsychopharmacol. 3(5/6):349–360, 1990.

Hartig, P. R., Kao, H.-T., Macchi, M., Adham, N., Zgombick, J., Weinshank, R. and Branchek, T.: The molecular biology of serotonin receptors: An overview. Neuropsychopharmacol. 3(5/6):335–347, 1990.

Herrick-Davis K. and Titeler, M.: Detection and characterization of the serotonin 5-HT$_{1D}$ receptor in rat and human brain. J. Neurochem. 50:1624–1631, 1988.

Hoyer, D.: Biochemical mechanisms of 5-HT receptor-effector coupling in peripheral tissues. In: Peripheral actions of 5-HT. (ed. Fozard, J. R.) Oxford:Oxford University Press, pp 72–99, 1989.

Humphrey, P. P. A., Feniuk, W., Perren, M. J., Beresford, I. J. M., Skingle, M. and Whalley, E. T.: Serotonin and migraine. Ann, N.Y. Acad. Sci. 600:587–600, 1990.

Insel, T. R., Mueller, E. A., Alterman, I., Linnoila, M. and Murphy, D. L.: Obsessive-compulsive disorder and serotonin: Is there a connection? Biol. Psychiat. 20:1774–1188, 1985.

Jimerson, D. C., Lesem, M. D., Hegg, A. P. and Brewerton, T. D.: Serotonin in human eating disorders. Ann, N.Y. Acad. Sci. 600:532–544, 1990.

Julius, D., MacDermott, A. B., Axel, R. and Jessell, T. M.: Molecular characterization of a functional cDNA encoding the serotonin 1C receptor. Science 241:558–564, 1988.

Leonhardt, S., Herrick-Davis, K. and Titeler, M.: Detection of a novel serotonin receptor subtype (5-HT1F, in human brain: Interaction with a GTP-binding protein. J. Neurochem. 53(2):465–471, 1989.

Levy, F. O., Gudermann, T., Birnbaumer, M., Kaumann, A. J., & Birnbaumer, L. Molecular cloning of a human gene (S31) encoding a novel serotonin receptor mediating inhibition of adenylyl cyclase. FEBS Lett. 296, 201–206, 1992.

Maniatis, T., Fritsch, E. F., and Sambrook, J. Molecular Cloning: A Laboratory Manual, Cold Spring Harbor Laboratory, Cold Spring Harbor, N.Y., 1982.

McAllister, G., Charlesworth, A., Snodin, C., Beer, M. S., Noble, A. J., Middlemiss, D. N., Iversen, L. L., & Whiting, P. Molecular cloning of a serotonin receptor from human brain (5-HT1E): A fifth 5HT1-like subtype. Proc. Natl. Acad. Sci. (USA), 89, 5517–5521, 1992.

McCabe, J. T. and Pfaff, D. W., in *Gene Probes* (Academic Press, San Diego) Conn, P. M. (ed.) pp. 98–126, 1989.

Moskowitz, M. A. Neurogenic versus vascular mechanisms of sumatriptan and ergot alkaloids in migraine. Trends Pharmacol. Sci. 13:307–311, 1992.

Osborne, N. N. and Hamon, M.: Neuronal serotonin. Chichester: John Wiley and Sons, Inc., 1988.

Peroutka, S. J.: Serotonin receptor subtypes: Basic and clinical aspects, New York: Wiley-Liss, Inc., 1991.

Peroutka, S. J. and Snyder, S. H.: Multiple serotonin receptors, differential binding of [$^3$H]5-hydroxytryptamine, [$^3$H]lysergic acid diethylamide and [$^3$H]spiroperidol. Mol. Pharmacol. 16:687–699, 1979.

Pritchett, D. B., Bach, A. W. J., Wozny, M., Taleb, O., Dal Toso, R., Shih, J. and Seeburg, P. H.: Structure and functional expression of cloned rat serotonin 5-HT2 receptor. EMBO J. 7:4135–4140, 1988.

Rapport, M. M., Green, A. A. and Page, I. H.: Purification of the the substance which is responsible for vasoconstrictor activity of serum. Fed. Proc. 6:184, 1947.

Rapport, M. M.: Serum vasoconstrictor (serotonin) V. Presence of creatinine in the complex. A proposed structure of the vasoconstrictor principle. J. Biol. Chem. 180:961–969, 1949.

Sambrook, J., Fritsch, E. F., & Maniatis, T., in *Molecular Cloning: A Laboratory Manual*; 2nd edition. (Cold Spring Harbor Laboratory, Cold Spring Harbor, N.Y.), pp. 7.19–7.22, 1989.

Sanders-Bush, E.: The Serotonin Receptors. Clifton, N.J.: Humana Press, 1988.

Sleight, A. J., Pierce, P. A., Schmidt, A. W., Hekmatpanah, C. R. and Peroutka, S. J.: The clinical utility of serotonin receptor active agents in neuropsychiatric disease. In: Serotonin receptor subtypes: Basic and clinical aspects. (ed. Peroutka, S. J.) New York: Wiley-Liss, Inc., pp 211–227, 1990.

Sumner, M. J. and Humphrey, P. P. A.: Sumatriptan (GR43175) inhibits cyclic-AMP accumulation in dog isolated saphenous vein. Br. J. Pharmacol. 99:219–220, 1990.

Zgombick, J. M., Schechter, L. E., Macchi, M., Hartig, P. R., Branchek, T. A., and Weinshank, R. L. The human gene S31 encodes the pharmacologically-defined serotonin 5-HT$_{1E}$ receptor. Mol. Pharmacol., 42, 180–185, 1992.

SEQUENCE LISTING

<160> NUMBER OF SEQ ID NOS: 13

<210> SEQ ID NO 1
<211> LENGTH: 1730
<212> TYPE: DNA
<213> ORGANISM: Homo sapiens

<400> SEQUENCE: 1

```
ttgcatgcct gcaggtcgac tctagaggat ccccgggtac cgagctcgaa t tcctttgtt      60 attttgtcat gcttcaagcc taggaaaagc ctaagcaaaa ctcttggtgg g ctctttgtt     120 acattccagc ctttgaataa gggcactggc tctatcagct ttgaatatat a actcaacta     180 gtcagtcagt agtactgaaa cagttgttac ggaggcctgc gttattgaga t cgggcctgc     240 cacacttta aactttttct gacatggaca aagagaaaaa ccaattctat a atggcagag     300 atttcactga gtaacaagct agagtatcat taaaaattgt tgtatttaac c tatatttta     360 agaaatgttt tggaagttac tggcttttt tactgttctc attaaatttc t taaataaaa     420 aggaaaacta aaaccttcaa tctgaacctc atttttttaa tctatagaat a ttctgggta     480 aacataacat acactttta aaaattattc tgaaaggaag agaaaagttc t tgaagcctt     540 ctctgaactg tttttctct tcccttgtta caggtatcca tttttcagct a tattaatct     600 tttaaaacaa agaaaatgga tttcttaaat tcatctgatc aaaacttgac c tcagaggaa     660 ctgttaaaca gaatgccatc caaaattctg gtgtccctca ctctgtctgg g ctggcactg     720 atgacaacaa ctatcaactc ccttgtgatc gctgcaatta ttgtgacccg g aagctgcac     780 catccagcca attatttaat ttgttccctt gcagtcacag attttcttgt g gctgtcctg     840
```

```
gtgatgccct tcagcattgt gtatattgtg agagagagct ggattatggg g caagtggtc    900
tgtgacattt ggctgagtgt tgacattacc tgctgcacgt gctccatctt g catctctca    960
gctatagctt tggatcggta tcgagcaatc acagatgctg ttgagtatgc c aggaaaagg   1020
actccaaagc atgctggcat tatgattaca atagtttgga ttatatctgt t tttatctct   1080
atgcctcctc tattctggag gcaccaagga actagcagag atgatgaatg c atcatcaag   1140
cacgaccaca ttgtttccac catttactca acatttggag ctttctacat c ccactggca   1200
ttgattttga tcctttacta caaaatatat agagcagcaa agacattata c cacaagaga   1260
caagcaagta ggattgcaaa ggaggaggtg aatggccaag tccttttgga g agtggtgag   1320
aaaagcacta aatcagtttc cacatcctat gtactagaaa agtctttatc t gacccatca   1380
acagactttg ataaaattca tagcacagtg agaagtctca ggtctgaatt c aagcatgag   1440
aaatcttgga gaaggcaaaa gatctcaggt acaagagaac ggaaagcagc c actaccctg   1500
ggattaatct tgggtgcatt tgtaatatgt tggcttcctt ttttgtaaa a gaattagtt   1560
gttaatgtct gtgacaaatg taaaatttct gaagaaatgt ccaattttt g gcatggctt   1620
gggtatctca attcccttat aaatccactg atttacacaa tctttaatga a gacttcaag   1680
aaagcattcc aaaagcttgt gcgatgtcga tgttagtttt aaaaatgttt             1730
```

<210> SEQ ID NO 2
<211> LENGTH: 366
<212> TYPE: PRT
<213> ORGANISM: Homo sapiens

<400> SEQUENCE: 2

```
Met Asp Phe Leu Asn Ser Ser Asp Gln Asn L eu Thr Ser Glu Glu Leu
  1               5                  10                  15

Leu Asn Arg Met Pro Ser Lys Ile Leu Val S er Leu Thr Leu Ser Gly
             20                  25                  30

Leu Ala Leu Met Thr Thr Thr Ile Asn Ser L eu Val Ile Ala Ala Ile
         35                  40                  45

Ile Val Thr Arg Lys Leu His His Pro Ala A sn Tyr Leu Ile Cys Ser
     50                  55                  60

Leu Ala Val Thr Asp Phe Leu Val Ala Val L eu Val Met Pro Phe Ser
 65                  70                  75                  80

Ile Val Tyr Ile Val Arg Glu Ser Trp Ile M et Gly Gln Val Val Cys
                 85                  90                  95

Asp Ile Trp Leu Ser Val Asp Ile Thr Cys C ys Thr Cys Ser Ile Leu
            100                 105                 110

His Leu Ser Ala Ile Ala Leu Asp Arg Tyr A rg Ala Ile Thr Asp Ala
        115                 120                 125

Val Glu Tyr Ala Arg Lys Arg Thr Pro Lys H is Ala Gly Ile Met Ile
    130                 135                 140

Thr Ile Val Trp Ile Ile Ser Val Phe Ile S er Met Pro Pro Leu Phe
145                 150                 155                 160

Trp Arg His Gln Gly Thr Ser Arg Asp Asp G lu Cys Ile Ile Lys His
                165                 170                 175

Asp His Ile Val Ser Thr Ile Tyr Ser Thr P he Gly Ala Phe Tyr Ile
            180                 185                 190

Pro Leu Ala Leu Ile Leu Ile Leu Tyr Tyr L ys Ile Tyr Arg Ala Ala
        195                 200                 205

Lys Thr Leu Tyr His Lys Arg Gln Ala Ser A rg Ile Ala Lys Glu Glu
    210                 215                 220
```

```
Val Asn Gly Gln Val Leu Leu Glu Ser Gly Glu Lys Ser Thr Lys Ser
225                 230                 235                 240

Val Ser Thr Ser Tyr Val Leu Glu Lys Ser Leu Ser Asp Pro Ser Thr
                245                 250                 255

Asp Phe Asp Lys Ile His Ser Thr Val Arg Ser Leu Arg Ser Glu Phe
                260                 265                 270

Lys His Glu Lys Ser Trp Arg Arg Gln Lys Ile Ser Gly Thr Arg Glu
                275                 280                 285

Arg Lys Ala Ala Thr Thr Leu Gly Leu Ile Leu Gly Ala Phe Val Ile
                290                 295                 300

Cys Trp Leu Pro Phe Phe Val Lys Glu Leu Val Val Asn Val Cys Asp
305                 310                 315                 320

Lys Cys Lys Ile Ser Glu Glu Met Ser Asn Phe Leu Ala Trp Leu Gly
                325                 330                 335

Tyr Leu Asn Ser Leu Ile Asn Pro Leu Ile Tyr Thr Ile Phe Asn Glu
                340                 345                 350

Asp Phe Lys Lys Ala Phe Gln Lys Leu Val Arg Cys Arg Cys
                355                 360             365

<210> SEQ ID NO 3
<211> LENGTH: 422
<212> TYPE: PRT
<213> ORGANISM: Homo sapiens

<400> SEQUENCE: 3

Met Asp Val Leu Ser Pro Gly Gln Gly Asn Asn Thr Thr Ser Pro Pro
1               5                   10                  15

Ala Pro Phe Glu Thr Gly Gly Asn Thr Thr Gly Ile Ser Asp Val Thr
                20                  25                  30

Val Ser Tyr Gln Val Ile Thr Ser Leu Leu Leu Gly Thr Leu Ile Phe
            35                  40                  45

Cys Ala Val Leu Gly Asn Ala Cys Val Val Ala Ala Ile Ala Leu Glu
        50                  55                  60

Arg Ser Leu Gln Asn Val Ala Asn Tyr Leu Ile Gly Ser Leu Ala Val
65              70                  75                  80

Thr Asp Leu Met Val Ser Val Leu Val Leu Pro Met Ala Ala Leu Tyr
                85                  90                  95

Gln Val Leu Asn Lys Trp Thr Leu Gly Gln Val Thr Cys Asp Leu Phe
                100                 105                 110

Ile Ala Leu Asp Val Leu Cys Cys Thr Ser Ser Ile Leu His Leu Cys
            115                 120                 125

Ala Ile Ala Leu Asp Arg Tyr Trp Ala Ile Thr Asp Pro Ile Asp Tyr
        130                 135                 140

Val Asn Lys Arg Thr Pro Arg Arg Ala Ala Leu Ile Ser Leu Thr
145                 150                 155                 160

Trp Leu Ile Gly Phe Leu Ile Ser Ile Pro Pro Met Leu Gly Trp Arg
                165                 170                 175

Thr Pro Glu Asp Arg Ser Asp Pro Asp Ala Cys Thr Ile Ser Lys Asp
                180                 185                 190

His Gly Tyr Thr Ile Tyr Ser Thr Phe Gly Ala Phe Tyr Ile Pro Leu
            195                 200                 205

Leu Leu Met Leu Val Leu Tyr Gly Arg Ile Phe Arg Ala Ala Arg Phe
        210                 215                 220

Arg Ile Arg Lys Thr Val Lys Lys Val Glu Lys Thr Gly Ala Asp Thr
225                 230                 235                 240
```

-continued

```
Arg His Gly Ala Ser Pro Ala Pro Gln Pro Lys Lys Ser Val Asn Gly
                245                 250                 255

Glu Ser Gly Ser Arg Asn Trp Arg Leu Gly Val Glu Ser Lys Ala Gly
            260                 265                 270

Gly Ala Leu Cys Ala Asn Gly Ala Val Arg Gln Gly Asp Asp Gly Ala
        275                 280                 285

Ala Leu Glu Val Ile Glu Val His Arg Val Gly Asn Ser Lys Glu His
    290                 295                 300

Leu Pro Leu Pro Ser Glu Ala Gly Pro Thr Pro Cys Ala Pro Ala Ser
305                 310                 315                 320

Phe Glu Arg Lys Asn Glu Arg Asn Ala Glu Ala Lys Arg Lys Met Ala
                325                 330                 335

Leu Ala Arg Glu Arg Lys Thr Val Lys Thr Leu Gly Ile Ile Met Gly
            340                 345                 350

Thr Phe Ile Leu Cys Trp Leu Pro Phe Phe Ile Val Ala Leu Val Leu
        355                 360                 365

Pro Phe Cys Glu Ser Ser Cys His Met Pro Thr Leu Leu Gly Ala Ile
    370                 375                 380

Ile Asn Trp Leu Gly Tyr Ser Asn Ser Leu Leu Asn Pro Val Ile Tyr
385                 390                 395                 400

Ala Tyr Phe Asn Lys Asp Phe Gln Asn Ala Phe Lys Lys Ile Ile Lys
                405                 410                 415

Cys Leu Phe Cys Arg Gln
            420

<210> SEQ ID NO 4
<211> LENGTH: 460
<212> TYPE: PRT
<213> ORGANISM: Homo sapiens

<400> SEQUENCE: 4

Met Val Asn Leu Gly Asn Ala Val Arg Ser Leu Leu Met His Leu Ile
 1               5                  10                  15

Gly Leu Leu Val Trp Gln Phe Asp Ile Ser Ile Ser Pro Val Ala Ala
            20                  25                  30

Ile Val Thr Asp Thr Phe Asn Ser Ser Asp Gly Gly Arg Leu Phe Gln
        35                  40                  45

Phe Pro Asp Gly Val Gln Asn Trp Pro Ala Leu Ser Ile Val Val Ile
    50                  55                  60

Ile Ile Met Thr Ile Gly Gly Asn Ile Leu Val Ile Met Ala Val Ser
65                  70                  75                  80

Met Glu Lys Lys Leu His Asn Ala Thr Asn Tyr Phe Leu Met Ser Leu
                85                  90                  95

Ala Ile Ala Asp Met Leu Val Gly Leu Leu Val Met Pro Leu Ser Leu
            100                 105                 110

Leu Ala Ile Leu Tyr Asp Tyr Val Trp Pro Leu Pro Arg Tyr Leu Cys
        115                 120                 125

Pro Val Trp Ile Ser Leu Asp Val Leu Phe Ser Thr Ala Ser Ile Met
    130                 135                 140

His Leu Cys Ala Ile Ser Leu Asp Arg Tyr Val Ala Ile Arg Asn Pro
145                 150                 155                 160

Ile Glu His Ser Arg Phe Asn Ser Arg Thr Lys Ala Ile Met Lys Ile
                165                 170                 175

Ala Ile Val Trp Ala Ile Ser Ile Gly Val Ser Val Pro Ile Pro Val
            180                 185                 190
```

```
Ile Gly Leu Arg Asp Glu Ser Lys Val Phe Val Asn Asn Thr Thr Cys
            195                 200                 205

Val Leu Asn Asp Pro Asn Phe Val Leu Ile Gly Ser Phe Val Ala Phe
    210                 215                 220

Phe Ile Pro Leu Thr Ile Met Val Ile Thr Tyr Phe Leu Thr Ile Tyr
225                 230                 235                 240

Val Leu Arg Arg Gln Thr Leu Met Leu Leu Arg Gly His Thr Glu Glu
                245                 250                 255

Glu Leu Ala Asn Met Ser Leu Asn Phe Leu Asn Cys Cys Cys Lys Lys
            260                 265                 270

Asn Gly Gly Glu Glu Asn Ala Pro Asn Pro Asn Pro Asp Gln Lys
        275                 280                 285

Pro Arg Arg Lys Lys Lys Glu Lys Arg Pro Arg Gly Thr Met Gln Ala
290                 295                 300

Ile Asn Asn Glu Lys Lys Ala Ser Lys Val Leu Gly Ile Val Phe Phe
305                 310                 315                 320

Val Phe Leu Ile Met Trp Cys Pro Phe Phe Ile Thr Asn Ile Leu Ser
                325                 330                 335

Val Leu Cys Gly Lys Ala Cys Asn Gln Lys Leu Met Glu Lys Leu Leu
            340                 345                 350

Asn Val Phe Val Trp Ile Gly Tyr Val Cys Ser Gly Ile Asn Pro Leu
        355                 360                 365

Val Tyr Thr Leu Phe Asn Lys Ile Tyr Arg Arg Ala Phe Ser Lys Tyr
370                 375                 380

Leu Arg Cys Asp Tyr Lys Pro Asp Lys Lys Pro Pro Val Arg Gln Ile
385                 390                 395                 400

Pro Arg Val Ala Ala Thr Ala Leu Ser Gly Arg Glu Leu Asn Val Asn
                405                 410                 415

Ile Tyr Arg His Thr Asn Glu Arg Val Ala Arg Lys Ala Asn Asp Pro
            420                 425                 430

Glu Pro Gly Ile Glu Met Gln Val Gly Asn Leu Glu Leu Pro Val Asn
        435                 440                 445

Pro Ser Asn Val Val Ser Glu Arg Ile Ser Ser Val
450                 455                 460

<210> SEQ ID NO 5
<211> LENGTH: 376
<212> TYPE: PRT
<213> ORGANISM: Homo sapiens

<400> SEQUENCE: 5

Met Ser Pro Leu Asn Gln Ser Ala Glu Gly Leu Pro Gln Glu Ala Ser
1               5                   10                  15

Asn Arg Ser Leu Asn Ala Thr Glu Thr Ser Glu Ala Trp Asp Pro Arg
            20                  25                  30

Thr Leu Gln Ala Leu Lys Ile Ser Leu Ala Val Val Leu Ser Val Ile
        35                  40                  45

Thr Leu Ala Thr Val Leu Ser Asn Ala Phe Val Leu Thr Thr Ile Leu
    50                  55                  60

Leu Thr Arg Lys Leu His Thr Pro Ala Asn Tyr Leu Ile Gly Ser Leu
65                  70                  75                  80

Ala Thr Thr Asp Leu Leu Val Ser Ile Leu Val Met Pro Ile Ser Met
                85                  90                  95

Ala Tyr Thr Ile Thr His Thr Trp Asn Phe Gly Gln Ile Leu Cys Asp
            100                 105                 110
```

-continued

```
Ile Trp Leu Ser Ser Asp Ile Thr Cys Cys Thr Ala Ser Ile Leu His
        115                 120                 125
Leu Cys Val Ile Ala Leu Asp Arg Tyr Trp Ala Ile Thr Asp Ala Leu
130                 135                 140
Glu Tyr Ser Lys Arg Arg Thr Ala Gly His Ala Ala Thr Met Ile Ala
145                 150                 155                 160
Ile Val Trp Ala Ile Ser Ile Cys Ile Ser Ile Pro Pro Leu Phe Trp
                165                 170                 175
Arg Gln Ala Lys Ala Gln Glu Glu Met Ser Asp Cys Leu Val Asn Thr
                180                 185                 190
Ser Gln Ile Ser Tyr Thr Ile Tyr Ser Thr Cys Gly Ala Phe Tyr Ile
                195                 200                 205
Pro Ser Val Leu Leu Ile Ile Leu Tyr Gly Arg Ile Tyr Arg Ala Ala
        210                 215                 220
Arg Asn Arg Ile Leu Asn Pro Pro Ser Leu Tyr Gly Lys Arg Phe Thr
225                 230                 235                 240
Thr Ala His Leu Ile Thr Gly Ser Gly Ser Ser Leu Cys Ser Leu Asn
                245                 250                 255
Ser Ser Leu His Glu Gly His Ser His Ser Ala Gly Ser Pro Leu Phe
                260                 265                 270
Phe Asn His Val Lys Ile Lys Leu Ala Asp Ser Ala Leu Glu Arg Lys
        275                 280                 285
Arg Ile Ser Ala Ala Arg Glu Arg Lys Ala Thr Lys Ile Leu Gly Ile
290                 295                 300
Ile Leu Gly Ala Phe Ile Ile Cys Trp Leu Pro Phe Phe Val Val Ser
305                 310                 315                 320
Leu Val Leu Pro Ile Cys Arg Asp Ser Cys Trp Ile His Pro Gly Leu
                325                 330                 335
Phe Asp Phe Phe Thr Trp Leu Gly Tyr Leu Asn Ser Leu Ile Asn Pro
                340                 345                 350
Ile Ile Tyr Thr Val Phe Asn Glu Glu Phe Arg Gln Ala Phe Gln Lys
        355                 360                 365
Ile Val Pro Phe Arg Lys Ala Ser
370                 375

<210> SEQ ID NO 6
<211> LENGTH: 390
<212> TYPE: PRT
<213> ORGANISM: Homo sapiens

<400> SEQUENCE: 6

Met Glu Glu Pro Gly Ala Gln Cys Ala Pro Pro Pro Pro Ala Gly Ser
1               5                   10                  15
Glu Thr Trp Val Pro Gln Ala Asn Leu Ser Ser Ala Pro Ser Gln Asn
                20                  25                  30
Cys Ser Ala Lys Asp Tyr Ile Tyr Gln Asp Ser Ile Ser Leu Pro Trp
            35                  40                  45
Lys Val Leu Leu Val Met Leu Leu Ala Leu Ile Thr Leu Ala Thr Thr
        50                  55                  60
Leu Ser Asn Ala Phe Val Ile Ala Thr Val Tyr Arg Thr Arg Lys Leu
65                  70                  75                  80
His Thr Pro Ala Asn Tyr Leu Ile Ala Ser Leu Ala Val Thr Asp Leu
                85                  90                  95
Leu Val Ser Ile Leu Val Met Pro Ile Ser Thr Met Tyr Thr Val Thr
            100                 105                 110
```

```
Gly Arg Trp Thr Leu Gly Gln Val Val Cys Asp Phe Trp Leu Ser Ser
            115                 120                 125

Asp Ile Thr Cys Cys Thr Ala Ser Ile Leu His Leu Cys Val Ile Ala
130                 135                 140

Leu Asp Arg Tyr Trp Ala Ile Thr Asp Val Ala Glu Tyr Ser Ala Lys
145                 150                 155                 160

Arg Thr Pro Lys Arg Ala Ala Val Met Ile Ala Leu Val Trp Val Phe
            165                 170                 175

Ser Ile Ser Ile Ser Leu Pro Pro Phe Phe Trp Arg Gln Ala Lys Ala
            180                 185                 190

Glu Glu Glu Val Ser Glu Cys Val Val Asn Thr Asp His Ile Leu Tyr
            195                 200                 205

Thr Val Tyr Ser Thr Val Gly Ala Phe Tyr Phe Pro Thr Leu Leu Leu
            210                 215                 220

Ile Ala Leu Tyr Gly Arg Ile Tyr Val Glu Ala Arg Ser Arg Ile Leu
225                 230                 235                 240

Lys Gln Thr Pro Asn Arg Thr Gly Lys Arg Leu Thr Arg Ala Gln Leu
            245                 250                 255

Ile Thr Asp Ser Pro Gly Ser Thr Ser Ser Val Thr Ser Ile Asn Ser
            260                 265                 270

Arg Val Pro Asp Val Pro Ser Glu Ser Gly Ser Pro Val Tyr Val Asn
            275                 280                 285

Gln Val Lys Val Arg Val Ser Asp Ala Leu Leu Glu Lys Lys Lys Leu
            290                 295                 300

Met Ala Ala Arg Glu Arg Lys Ala Thr Lys Thr Leu Gly Ile Ile Leu
305                 310                 315                 320

Gly Ala Phe Ile Val Cys Trp Leu Pro Phe Phe Ile Ile Ser Leu Val
            325                 330                 335

Met Pro Ile Cys Lys Asp Ala Cys Trp Phe His Leu Ala Ile Phe Asp
            340                 345                 350

Phe Phe Thr Trp Leu Gly Tyr Leu Asn Leu Ile Asn Pro Ile Ile Tyr
            355                 360                 365

Thr Met Ser Asn Glu Asp Phe Lys Gln Ala Phe His Lys Leu Ile Arg
            370                 375                 380

Phe Ile Cys Cys Thr Ser
385                 390

<210> SEQ ID NO 7
<211> LENGTH: 366
<212> TYPE: PRT
<213> ORGANISM: Homo sapiens

<400> SEQUENCE: 7

Met Asp Phe Leu Asn Ser Ser Asp Gln Asn Leu Thr Ser Glu Glu Leu
1               5                   10                  15

Leu Asn Arg Met Pro Ser Lys Ile Leu Val Ser Leu Thr Leu Ser Gly
            20                  25                  30

Leu Ala Leu Met Thr Thr Thr Ile Asn Ser Leu Val Ile Ala Ala Ile
            35                  40                  45

Ile Val Thr Arg Lys Leu His His Pro Ala Asn Tyr Leu Ile Cys Ser
50                  55                  60

Leu Ala Val Thr Asp Phe Leu Val Ala Val Leu Val Met Pro Phe Ser
65                  70                  75                  80

Ile Val Tyr Ile Val Arg Glu Ser Trp Ile Met Gly Gln Val Val Cys
            85                  90                  95
```

```
Asp Ile Trp Leu Ser Val Asp Ile Thr Cys Cys Thr Cys Ser Ile Leu
            100                 105                 110

His Leu Ser Ala Ile Ala Leu Asp Arg Tyr Arg Ala Ile Thr Asp Ala
            115                 120                 125

Val Glu Tyr Ala Arg Lys Arg Thr Pro Lys His Ala Gly Ile Met Ile
            130                 135                 140

Thr Ile Val Trp Ile Ile Ser Val Phe Ile Ser Met Pro Pro Leu Phe
145                 150                 155                 160

Trp Arg His Gln Gly Thr Ser Arg Asp Asp Glu Cys Ile Ile Lys His
                165                 170                 175

Asp His Ile Val Ser Thr Ile Tyr Ser Thr Phe Gly Ala Phe Tyr Ile
            180                 185                 190

Pro Leu Ala Leu Ile Leu Ile Leu Tyr Tyr Lys Ile Tyr Arg Ala Ala
            195                 200                 205

Lys Thr Leu Tyr His Lys Arg Gln Ala Ser Arg Ile Ala Lys Glu Glu
210                 215                 220

Val Asn Gly Gln Val Leu Leu Glu Ser Gly Glu Lys Ser Thr Lys Ser
225                 230                 235                 240

Val Ser Thr Ser Tyr Val Leu Glu Lys Ser Leu Ser Asp Pro Ser Thr
                245                 250                 255

Asp Phe Asp Lys Ile His Ser Thr Val Arg Ser Leu Arg Ser Glu Phe
            260                 265                 270

Lys His Glu Lys Ser Trp Arg Arg Gln Lys Ile Ser Gly Thr Arg Glu
            275                 280                 285

Arg Lys Ala Ala Thr Thr Leu Gly Leu Ile Leu Gly Ala Phe Val Ile
            290                 295                 300

Cys Trp Leu Pro Phe Phe Val Lys Glu Leu Val Val Asn Val Cys Asp
305                 310                 315                 320

Lys Cys Lys Ile Ser Glu Glu Met Ser Asn Phe Leu Ala Trp Leu Gly
                325                 330                 335

Tyr Leu Asn Ser Leu Ile Asn Pro Leu Ile Tyr Thr Ile Phe Asn Glu
            340                 345                 350

Asp Phe Lys Lys Ala Phe Gln Lys Leu Val Arg Cys Arg Cys
            355                 360                 365

<210> SEQ ID NO 8
<211> LENGTH: 470
<212> TYPE: PRT
<213> ORGANISM: Homo sapiens

<400> SEQUENCE: 8

Met Asp Ile Leu Cys Glu Glu Asn Thr Ser Leu Ser Ser Thr Thr Asn
1               5                   10                  15

Ser Leu Met Gln Leu Asn Asp Asp Thr Arg Leu Tyr Ser Asn Asp Phe
            20                  25                  30

Asn Ser Gly Glu Ala Asn Thr Ser Asp Ala Phe Asn Trp Thr Val Asp
            35                  40                  45

Ser Glu Asn Arg Thr Asn Leu Ser Cys Glu Gly Cys Leu Ser Pro Ser
        50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110
```

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Gly Thr Arg Ala Lys Leu Ala Ser Phe Ser Phe Leu Pro Gln Ser Ser
        275                 280                 285

Leu Ser Ser Glu Lys Leu Phe Gln Arg Ser Ile His Arg Glu Pro Gly
290                 295                 300

Ser Tyr Thr Gly Arg Arg Thr Met Gln Ser Ile Ser Asn Glu Gln Lys
305                 310                 315                 320

Ala Cys Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
            340                 345                 350

Cys Asn Glu Asp Val Ile Gly Ala Leu Leu Asn Val Phe Val Trp Ile
        355                 360                 365

Gly Tyr Leu Ser Ser Ala Val Asn Pro Leu Val Tyr Thr Leu Phe Asn
    370                 375                 380

Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
                405                 410                 415

Leu Ala Tyr Lys Ser Ser Gln Leu Gln Met Gly Gln Lys Lys Ser Lys
            420                 425                 430

Gln Asp Ala Lys Thr Thr Asp Asn Asp Cys Ser Met Val Ala Leu Gly
        435                 440                 445

Lys Gln His Ser Glu Glu Ala Ser Lys Asp Asn Ser Asp Gly Val Asn
    450                 455                 460

Glu Lys Val Ser Cys Val
465                 470

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: primer
      /probe

```
<400> SEQUENCE: 9
tctcaccact ctccaaaagg acttggccat tcacctcctc ctttg            45

<210> SEQ ID NO 10
<211> LENGTH: 24
<212> TYPE: DNA
<213> ORGANISM: Artificial Sequence
<220> FEATURE:
<223> OTHER INFORMATION: Description of Artificial  Sequence: primer
      /probe

<400> SEQUENCE: 10
tctattctgg aggcaccaag gaac                                    24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial  Sequence: primer
      /probe

<400> SEQUENCE: 11
tgttgatggg tcagataaag actt                                    24

<210> SEQ ID NO 12
<211> LENGTH: 45
<212> TYPE: DNA
<213> ORGANISM: Artificial Sequence
<220> FEATURE:
<223> OTHER INFORMATION: Description of Artificial  Sequence: primer
      /probe

<400> SEQUENCE: 12
gtgatgcttg atgatgcact catcatctcg gcttgtcccc tggtg            45

<210> SEQ ID NO 13
<211> LENGTH: 45
<212> TYPE: DNA
<213> ORGANISM: Artificial Sequence
<220> FEATURE:
<223> OTHER INFORMATION: Description of Artificial  Sequence: primer
      /probe

<400> SEQUENCE: 13
tagcagttcc tctgaggtca agttttgatc agaagagttt aagaa            45
```

What is claimed is:

1. A method of obtaining a composition which comprises determining whether a chemical compound binds to a human 5-$HT_{1F}$ receptor expressed on the surface of a mammalian cell comprising a vector adapted for expressing the receptor in the cell, and if the compound binds to the receptor, admixing the compound with a carrier, wherein the human 5-$HT_{1F}$ receptor (a) has an amino acid sequence identical to the amino acid sequence shown in FIG. 1 (SEQ ID NO. 2) or (b) is encoded by a nucleic acid sequence identical to the receptor-encoding nucleic acid sequence contained in plasmid pMO5-hl16a (ATCC Accession No. 75175).

2. A method of obtaining a composition which comprises determining whether a chemical compound binds to and activates a human 5-$HT_{1F}$ receptor expressed on the surface of a mammalian cell, and if the compound binds to and activates the receptor, admixing the compound with a carrier, wherein the mammalian cell comprises a vector which expresses the receptor; wherein the human 5-$HT_{1F}$ receptor (a) has an amino acid sequence identical to the amino acid sequence shown in FIG. 1 (SEQ ID NO. 2) or (b) is encoded by a nucleic acid whose sequence is identical to the receptor-encoding nucleic acid sequence contained in plasmid pMO5-hl16a (ATCC Accession No. 75175); and wherein activation of the human 5-$HT_{1F}$ receptor is determined by measuring cAMP formation.

3. A method of obtaining a composition which comprises determining whether a chemical compound binds to and prevents the activation of a human 5-$HT_{1F}$ receptor expressed on the surface of a mammalian cell, and if the compound binds to and prevents the activation of the receptor, admixing the compound with a carrier, wherein the mammalian cell comprises a vector which expresses the receptor; wherein the human 5-$HT_{1F}$ receptor (a) has an amino acid sequence identical to the amino acid sequence shown in FIG. 1 (SEQ ID NO. 2) or (b) is encoded by a nucleic acid whose sequence is identical to the receptor-encoding nucleic acid sequence contained in plasmid pMO5-hl16a (ATCC Accession No. 75175); and wherein activation of the human 5-$HT_{1F}$ receptor is determined by measuring cAMP formation.

* * * * *